(12) United States Patent
Levine et al.

(10) Patent No.: US 10,080,841 B2
(45) Date of Patent: Sep. 25, 2018

(54) SYSTEMS AND METHODS FOR MONITORING, MANAGING, AND TREATING ASTHMA AND ANAPHYLAXIS

(71) Applicant: President and Fellows of Harvard College, Cambridge, MA (US)

(72) Inventors: Andy H. Levine, Newton, MA (US); Christoph Matthias Kanzler, Brookline, MA (US); Daniel Leo Miranda, Natick, MA (US); Joseph Mooney, Sudbury, MA (US); Huy Lam, Germantown, MD (US); John Osborne, Winchester, MA (US); Mustafa Karabas, Chestnut Hill, MA (US); Alan Dunne, Cambridge, MA (US); James Niemi, Concord, MA (US); Benjamin Matthews, Newton, MA (US); Donald E. Ingber, Boston, MA (US); Olivier Henry, Brookline, MA (US); Premananda Pai Indic, Whitehouse, TX (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/591,329

(22) Filed: May 10, 2017

(65) Prior Publication Data
US 2017/0239418 A1    Aug. 24, 2017

Related U.S. Application Data

(63) Continuation of application No. PCT/US2016/062920, filed on Nov. 18, 2016.
(Continued)

(51) Int. Cl.
*A61B 5/08* (2006.01)
*A61M 5/172* (2006.01)
(Continued)

(52) U.S. Cl.
CPC ......... *A61M 5/1723* (2013.01); *A61K 31/137* (2013.01); *A61M 5/14248* (2013.01);
(Continued)

(58) Field of Classification Search
CPC .... A61M 2005/206; A61M 2005/2013; A61M 5/20; A61M 5/2033
See application file for complete search history.

(56) References Cited

U.S. PATENT DOCUMENTS

| 6,165,155 A | 12/2000 | Jacobsen |
| 6,425,887 B1 | 7/2002 | McGuckin |

(Continued)

FOREIGN PATENT DOCUMENTS

| EP | 2468340 A1 | 6/2012 |
| EP | 2698180 A1 | 2/2014 |

(Continued)

OTHER PUBLICATIONS

Aibi, "Anaphylaxis Prevention System for Children," retrieved from the Internet: http://madebychip.com/aibi/html on Jan. 10, 2017 (27 pages).
(Continued)

*Primary Examiner* — Puya Agahi
(74) *Attorney, Agent, or Firm* — Nixon Peabody LLP

(57) ABSTRACT

A physiologic sensor module includes at least one wearable sensor that is configured for wearing on a human body part and for measuring at least one biological signal. The module further includes at least one controller communicatively coupled to the wearable sensor and configured to receive the biological signal from the wearable sensor. The controller is
(Continued)

further configured to process the biological signal in real-time, extract one or more clinical features from the biological signal, and based on the clinical features, determine detection of anaphylaxis.

16 Claims, 28 Drawing Sheets

Related U.S. Application Data

(60) Provisional application No. 62/257,190, filed on Nov. 18, 2015.

(51) Int. Cl.
*A61M 5/20* (2006.01)
*A61M 5/142* (2006.01)
*A61M 37/00* (2006.01)
*A61K 31/137* (2006.01)
*A61B 5/145* (2006.01)
*A61B 5/1486* (2006.01)
*A61B 5/113* (2006.01)
*A61B 5/00* (2006.01)

(52) U.S. Cl.
CPC ...... *A61M 5/2053* (2013.01); *A61M 37/0015* (2013.01); *A61B 5/0826* (2013.01); *A61B 5/113* (2013.01); *A61B 5/1451* (2013.01); *A61B 5/1486* (2013.01); *A61B 5/14546* (2013.01); *A61B 5/411* (2013.01); *A61M 2005/1726* (2013.01); *A61M 2005/206* (2013.01); *A61M 2205/18* (2013.01); *A61M 2205/50* (2013.01); *A61M 2205/581* (2013.01); *A61M 2205/587* (2013.01); *A61M 2205/8206* (2013.01); *A61M 2230/005* (2013.01); *A61M 2230/04* (2013.01); *A61M 2230/30* (2013.01); *A61M 2230/50* (2013.01); *A61M 2230/63* (2013.01); *A61M 2230/65* (2013.01)

(56) References Cited

U.S. PATENT DOCUMENTS

| | | | |
|---|---|---|---|
| 6,485,461 | B1 | 11/2002 | Mason |
| 6,575,931 | B1 | 6/2003 | Ponzi |
| 6,656,158 | B2 | 12/2003 | Mahoney |
| 6,656,159 | B2 | 12/2003 | Flaherty |
| 6,658,287 | B1 | 12/2003 | Litt |
| 6,669,669 | B2 | 12/2003 | Flaherty |
| 6,692,457 | B2 | 2/2004 | Flaherty |
| 6,699,218 | B2 | 3/2004 | Flaherty |
| 6,723,072 | B2 | 4/2004 | Flaherty |
| 6,740,059 | B2 | 5/2004 | Flaherty |
| 6,749,587 | B2 | 6/2004 | Flaherty |
| 6,768,425 | B2 | 7/2004 | Flaherty |
| 6,800,070 | B2 | 10/2004 | Mazidji |
| 6,830,558 | B2 | 12/2004 | Flaherty |
| 6,960,192 | B1 | 11/2005 | Flaherty |
| 7,018,360 | B2 | 3/2006 | Flaherty |
| 7,029,455 | B2 | 4/2006 | Flaherty |
| 7,077,810 | B2 | 7/2006 | Lange |
| 7,128,727 | B2 | 10/2006 | Flaherty |
| 7,134,999 | B2 | 11/2006 | Brauker |
| 7,144,384 | B2 | 12/2006 | Gorman |
| 7,250,037 | B2 | 7/2007 | Shermer |
| 7,303,549 | B2 | 12/2007 | Flaherty |
| 7,435,240 | B2 | 10/2008 | Barkhahn |
| 7,524,304 | B2 | 4/2009 | Genosar |
| 7,678,079 | B2 | 3/2010 | Shermer |
| 7,706,878 | B2 | 4/2010 | Freeman |
| 7,749,194 | B2 | 7/2010 | Edwards |
| 7,857,131 | B2 | 12/2010 | Vedrine |
| 7,885,697 | B2 | 2/2011 | Brister |
| 7,918,825 | B2 | 4/2011 | O'Connor |
| 7,946,984 | B2 | 5/2011 | Brister |
| 8,100,922 | B2 | 1/2012 | Griffith |
| 8,152,779 | B2 | 4/2012 | Cabiri |
| 8,157,769 | B2 | 4/2012 | Cabiri |
| 8,170,803 | B2 | 5/2012 | Kamath |
| 8,251,963 | B2 | 8/2012 | Chin |
| 8,280,475 | B2 | 10/2012 | Brister |
| 8,313,470 | B2 | 11/2012 | Abry |
| 8,328,420 | B2 | 12/2012 | Abreu |
| 8,348,898 | B2 | 1/2013 | Cabiri |
| 8,357,125 | B2 | 1/2013 | Grunhut |
| 8,366,668 | B2 | 2/2013 | Maritan |
| 8,376,954 | B2 | 2/2013 | Lange |
| 8,385,998 | B2 | 2/2013 | Zhang |
| 8,435,738 | B2 | 5/2013 | Holmes |
| 8,444,604 | B2 | 5/2013 | Cindrich |
| 8,463,350 | B2 | 6/2013 | Kamath |
| 8,465,455 | B2 | 6/2013 | Cabiri |
| 8,475,739 | B2 | 7/2013 | Holmes |
| 8,491,530 | B2 | 7/2013 | Maritan |
| 8,500,693 | B2 | 8/2013 | Maritan |
| 8,512,287 | B2 | 8/2013 | Cindrich |
| 8,515,516 | B2 | 8/2013 | Kamath |
| 8,529,447 | B2 | 9/2013 | Jain |
| 8,540,629 | B2 | 9/2013 | Jain |
| 8,568,359 | B2 | 10/2013 | Carrel |
| 8,571,625 | B2 | 10/2013 | Kamath |
| 8,608,707 | B2 | 12/2013 | Abry |
| 8,617,067 | B2 | 12/2013 | Jain |
| 8,622,899 | B2 | 1/2014 | Jain |
| 8,622,900 | B2 | 1/2014 | Jain |
| 8,622,901 | B2 | 1/2014 | Jain |
| 8,639,288 | B1 | 1/2014 | Friedman |
| D702,834 | S | 4/2014 | Norton |
| 8,690,775 | B2 | 4/2014 | Brister |
| 8,690,827 | B2 | 4/2014 | Edwards |
| 8,725,462 | B2 | 5/2014 | Jain |
| 8,747,359 | B2 | 6/2014 | Pakter |
| D708,317 | S | 7/2014 | Schneider |
| 8,792,953 | B2 | 7/2014 | Brister |
| 8,814,828 | B2 | 8/2014 | Llewellyn-Hyde |
| 8,815,178 | B2 | 8/2014 | Bishop |
| 8,825,127 | B2 | 9/2014 | Kamath |
| 8,834,020 | B2 | 9/2014 | Abreu |
| 8,840,838 | B2 | 9/2014 | Holmes |
| 8,858,434 | B2 | 10/2014 | Kamath |
| 8,864,720 | B2 | 10/2014 | Smith |
| 8,915,849 | B2 | 12/2014 | Brauker |
| 8,915,882 | B2 | 12/2014 | Cabiri |
| 8,992,434 | B2 | 3/2015 | Halperin |
| 9,011,164 | B2 | 4/2015 | Filman |
| 9,055,901 | B2 | 6/2015 | Brister |
| 9,072,827 | B2 | 7/2015 | Cabiri |
| 9,072,837 | B2 | 7/2015 | Maritan |
| 9,078,626 | B2 | 7/2015 | Brister |
| 9,128,015 | B2 | 9/2015 | Holmes |
| 9,149,575 | B2 | 10/2015 | Cabiri |
| 9,166,313 | B2 | 10/2015 | Filman |
| 9,173,567 | B2 | 11/2015 | Jain |
| 9,173,997 | B2 | 11/2015 | Gross |
| 9,180,244 | B2 | 11/2015 | Anderson |
| 9,189,599 | B2 | 11/2015 | Adler |
| D747,799 | S | 1/2016 | Norton |
| 9,247,900 | B2 | 2/2016 | Brister |
| 9,250,229 | B2 | 2/2016 | Holmes |
| 9,259,532 | B2 | 2/2016 | Cabiri |
| 9,268,915 | B2 | 2/2016 | Holmes |
| 9,345,836 | B2 | 5/2016 | Cabiri |
| 9,358,103 | B1 | 6/2016 | Wortz |
| 9,364,606 | B2 | 6/2016 | Cindrich |
| 9,393,365 | B2 | 7/2016 | Cabiri |
| 9,398,856 | B2 | 7/2016 | Abreu |
| 9,414,777 | B2 | 8/2016 | Brister |
| 9,414,907 | B2 | 8/2016 | Wortz |
| 9,421,323 | B2 | 8/2016 | Cabiri |
| 9,451,910 | B2 | 9/2016 | Brister |
| 9,452,258 | B2 | 9/2016 | Dobbles |
| 9,452,259 | B2 | 9/2016 | Dobbles |

(56) References Cited

U.S. PATENT DOCUMENTS

| | | |
|---|---|---|
| 9,504,558 B2 | 11/2016 | Wortz |
| 9,517,127 B2 | 12/2016 | Wortz |
| 9,522,059 B2 | 12/2016 | Wortz |
| 9,542,826 B2 | 1/2017 | Edwards |
| 2004/0010207 A1 | 1/2004 | Flaherty |
| 2004/0076588 A1 | 4/2004 | Batycky |
| 2004/0092873 A1 | 5/2004 | Moberg |
| 2005/0171512 A1 | 8/2005 | Flaherty |
| 2005/0203461 A1 | 9/2005 | Flaherty |
| 2005/0238507 A1 | 10/2005 | Diianni |
| 2005/0240087 A1 | 10/2005 | Keenan |
| 2006/0041229 A1 | 2/2006 | Garibotto |
| 2006/0178633 A1 | 8/2006 | Garibotto |
| 2006/0282290 A1 | 12/2006 | Flaherty |
| 2007/0017533 A1 | 1/2007 | Wyrick |
| 2007/0067004 A1 | 3/2007 | Boveja |
| 2008/0033367 A1 | 2/2008 | Haury |
| 2008/0116647 A1 | 5/2008 | Anderson |
| 2008/0118405 A1 | 5/2008 | Conoci |
| 2008/0160492 A1 | 7/2008 | Campbell |
| 2008/0306436 A1* | 12/2008 | Edwards ............ A61M 5/19 604/67 |
| 2009/0054737 A1 | 2/2009 | Magar |
| 2009/0093793 A1 | 4/2009 | Gross |
| 2009/0105605 A1 | 4/2009 | Abreu |
| 2009/0124867 A1 | 5/2009 | Hirsh |
| 2009/0306741 A1 | 12/2009 | Hogle |
| 2009/0312817 A1 | 12/2009 | Hogle |
| 2010/0017141 A1 | 1/2010 | Campbell |
| 2010/0022992 A1 | 1/2010 | Genosar |
| 2010/0166802 A1* | 7/2010 | Caplan ............ A61K 39/35 424/257.1 |
| 2010/0318035 A1 | 12/2010 | Edwards |
| 2011/0098580 A1* | 4/2011 | Mikhail ............ A61B 5/0215 600/485 |
| 2012/0022499 A1 | 1/2012 | Anderson |
| 2012/0041364 A1 | 2/2012 | Smith |
| 2012/0103329 A1 | 5/2012 | Smith |
| 2012/0165634 A1 | 6/2012 | Lee |
| 2012/0165635 A1 | 6/2012 | Radhakrishnan |
| 2012/0233834 A1 | 9/2012 | Szechinski |
| 2012/0289788 A1 | 11/2012 | Jain |
| 2012/0289789 A1 | 11/2012 | Jain |
| 2012/0289790 A1 | 11/2012 | Jain |
| 2012/0289791 A1 | 11/2012 | Jain |
| 2012/0289792 A1 | 11/2012 | Jain |
| 2012/0289793 A1 | 11/2012 | Jain |
| 2012/0289794 A1 | 11/2012 | Jain |
| 2012/0290215 A1 | 11/2012 | Adler |
| 2012/0290266 A1 | 11/2012 | Jain |
| 2013/0068641 A1 | 3/2013 | Puglisi |
| 2013/0074614 A1 | 3/2013 | Holmes |
| 2013/0078149 A1 | 3/2013 | Holmes |
| 2013/0078624 A1 | 3/2013 | Holmes |
| 2013/0078625 A1 | 3/2013 | Holmes |
| 2013/0078733 A1 | 3/2013 | Holmes |
| 2013/0079236 A1 | 3/2013 | Holmes |
| 2013/0079599 A1 | 3/2013 | Holmes |
| 2013/0124039 A1 | 5/2013 | Abreu |
| 2013/0253472 A1 | 9/2013 | Cabiri |
| 2013/0273154 A1 | 10/2013 | Fayad |
| 2013/0309637 A1 | 11/2013 | Minvielle |
| 2013/0324820 A1 | 12/2013 | Petillo |
| 2014/0039383 A1 | 2/2014 | Dobbles |
| 2014/0073043 A1 | 3/2014 | Holmes |
| 2014/0114248 A1 | 4/2014 | DeSalvo |
| 2014/0114250 A1 | 4/2014 | DeSalvo |
| 2014/0114277 A1 | 4/2014 | Eggert |
| 2014/0142508 A1 | 5/2014 | Diianni |
| 2014/0148761 A1 | 5/2014 | Rotem |
| 2014/0148784 A1 | 5/2014 | Anderson |
| 2014/0163339 A1 | 6/2014 | Goldstein |
| 2014/0170735 A1 | 6/2014 | Holmes |
| 2014/0186238 A1 | 7/2014 | Holmes |
| 2014/0234949 A1 | 8/2014 | Wasson |
| 2014/0243749 A1 | 8/2014 | Edwards |
| 2014/0276586 A1 | 9/2014 | Swaney |
| 2014/0294951 A1 | 10/2014 | Fayad |
| 2014/0296089 A1 | 10/2014 | Holmes |
| 2014/0308661 A1 | 10/2014 | Holmes |
| 2014/0330335 A1 | 11/2014 | Errico |
| 2015/0011973 A1 | 1/2015 | Edwards |
| 2015/0030544 A1 | 1/2015 | Clark |
| 2015/0038907 A1 | 2/2015 | Rotem |
| 2015/0045718 A1 | 2/2015 | Shlomo |
| 2015/0057611 A1 | 2/2015 | Bureau |
| 2015/0094914 A1 | 4/2015 | Abreu |
| 2015/0125945 A1 | 5/2015 | Holmes |
| 2015/0126829 A1 | 5/2015 | Bernstein |
| 2015/0150453 A1 | 6/2015 | Abreu |
| 2015/0224253 A1 | 8/2015 | Cabiri |
| 2015/0257976 A1 | 9/2015 | Puglisi |
| 2015/0290391 A1 | 10/2015 | Schmid |
| 2015/0290453 A1 | 10/2015 | Tyler |
| 2015/0294551 A1 | 10/2015 | Edwards |
| 2015/0297833 A1 | 10/2015 | Henderson |
| 2015/0320588 A1 | 11/2015 | Connor |
| 2015/0338428 A1 | 11/2015 | Holmes |
| 2015/0366656 A1 | 12/2015 | Wortz |
| 2015/0366659 A1 | 12/2015 | Wortz |
| 2015/0368717 A1 | 12/2015 | Holmes |
| 2016/0003823 A1 | 1/2016 | Holmes |
| 2016/0007864 A1 | 1/2016 | Scharf |
| 2016/0008206 A1 | 1/2016 | Devanaboyina |
| 2016/0011215 A1 | 1/2016 | Holmes |
| 2016/0011225 A1 | 1/2016 | Holmes |
| 2016/0025760 A1 | 1/2016 | Holmes |
| 2016/0025763 A1 | 1/2016 | Holmes |
| 2016/0029963 A1* | 2/2016 | Hyde ............ A61B 5/1171 600/301 |
| 2016/0032361 A1 | 2/2016 | Holmes |
| 2016/0033544 A1 | 2/2016 | Holmes |
| 2016/0051806 A1 | 2/2016 | Goldsmith |
| 2016/0054343 A1 | 2/2016 | Holmes |
| 2016/0069919 A1 | 3/2016 | Holmes |
| 2016/0069920 A1 | 3/2016 | Holmes |
| 2016/0069921 A1 | 3/2016 | Holmes |
| 2016/0077015 A1 | 3/2016 | Holmes |
| 2016/0082189 A1 | 3/2016 | Anderson |
| 2016/0084863 A1 | 3/2016 | Holmes |
| 2016/0089089 A1* | 3/2016 | Kakkar ............ G06F 19/325 600/484 |
| 2016/0103123 A1 | 4/2016 | Holmes |
| 2016/0114163 A1 | 4/2016 | Franke |
| 2016/0124009 A1 | 5/2016 | Wasson |
| 2016/0135706 A1 | 5/2016 | Sullivan |
| 2016/0169880 A1 | 6/2016 | Holmes |
| 2016/0169923 A1 | 6/2016 | Holmes |
| 2016/0216286 A1 | 7/2016 | Holmes |
| 2016/0216287 A1 | 7/2016 | Holmes |
| 2016/0235524 A1 | 8/2016 | Wortz |
| 2016/0235908 A1 | 8/2016 | Schmid |
| 2016/0256260 A1 | 9/2016 | Wortz |
| 2016/0256262 A1 | 9/2016 | Wortz |
| 2016/0256263 A1 | 9/2016 | Wortz |
| 2016/0256267 A1 | 9/2016 | Wortz |
| 2016/0256315 A1 | 9/2016 | Wortz |
| 2016/0320381 A1 | 11/2016 | Holmes |
| 2016/0324463 A1 | 11/2016 | Simpson |
| 2016/0328990 A1 | 11/2016 | Simpson |
| 2016/0328991 A1 | 11/2016 | Simpson |
| 2016/0334119 A1 | 11/2016 | Cameron |
| 2016/0338825 A1 | 11/2016 | Wortz |
| 2016/0361496 A1 | 12/2016 | Guillermo |
| 2016/0370396 A1 | 12/2016 | Wasson |
| 2016/0377640 A1 | 12/2016 | Balwani |
| 2017/0000416 A1 | 1/2017 | EhrenKranz |

FOREIGN PATENT DOCUMENTS

| | | |
|---|---|---|
| EP | 2829290 A1 | 1/2015 |
| WO | WO 2002/028454 A2 | 4/2002 |
| WO | WO 2003/024504 A2 | 3/2003 |
| WO | WO 2003/103763 A1 | 12/2003 |

(56) References Cited

FOREIGN PATENT DOCUMENTS

| | | |
|---|---|---|
| WO | WO 2004/060436 A2 | 7/2004 |
| WO | WO 2004/098390 A2 | 11/2004 |
| WO | WO 2004/098454 A2 | 11/2004 |
| WO | WO 2005/046756 A1 | 5/2005 |
| WO | WO 2006/104806 A2 | 10/2006 |
| WO | WO 2007/010522 A1 | 1/2007 |
| WO | WO 2007/051139 A2 | 5/2007 |
| WO | WO 2008/129549 A1 | 10/2008 |
| WO | WO 2012/000570 A1 | 1/2012 |
| WO | WO 2012/152667 A1 | 11/2012 |
| WO | WO 2014/107408 A1 | 7/2014 |
| WO | WO 2015/024960 A1 | 2/2015 |
| WO | WO 2016/018148 A1 | 2/2016 |
| WO | WO 2016/062605 A1 | 4/2016 |
| WO | WO 2016/088119 A1 | 6/2016 |

OTHER PUBLICATIONS

Langan, M., M.D.; "The EpiBracelet—a Wearable, Portable and Fashionable Automatic Epinephrine Injection Device"; Aug. 16, 2015; retrieved from the Internet: http://www.slideshare.net/MichaelLangan/slideshelf, on Jan. 10, 2017 (55 pages).

Cash, K. et al.; "Phosphorescent nanosensors for in vivo tracking of histamine levels"; Anal. Chem. author manuscript, available in PMC Jul. 22, 2014; Anal. Chem. Jul. 2, 2013; 85(13): 6312-6318; DOI: 10.1021/ac400575u (17 pages).

Iwaki, S. et al.; "Real-Time Monitoring of Histamine Released from Rat Basophilic Leukemia (RBL-2H3) Cells with a Histamine Microsensor Using Recombinant Histamine Oxidase"; Anal. Biochem. 304, pp. 236-243; Jun. 2002 (9 pages).

Bozkurt, A. et al.; "New Devices, Wearable System Aim to Predict, Prevent Asthma Attacks"; Jun. 1, 2016; retrieved from the Internet: https://news.ncsu.edu/2016/06/wearable-tech-asthma-2106/, on Jan. 10, 2017 (7 pages).

Niwa, O. et al.; "Continuous measurement of histamine from rat basophilic leukemia cells (RBL-2H3) with an on-line sensor using histamine oxidase"; Sensors and Actuators B. 67, pp. 43-51; Aug. 2000 (10 pages).

Loughran, M.G. et al.; "Amperometric detection of histamine at a quinoprotein dehydrogenase enzyme electrode"; Elsevier Science Ltd.; Biosensors & Bioelectronics 10 (1995), pp. 569-576 (8 pages).

Zeng, K. et al.; "Amperometric Detection of Histamine with a Methylamine Dehydrogenase Polypyrrole-Based Sensor"; Anal. Chem., vol. 72, No. 10, pp. 2211-2215; May 15, 2000 (5 pages).

International Search Report and Written Opinion of International Searching Authority for PCT/US2016/062920 dated Feb. 6, 2017 (17 pages).

* cited by examiner

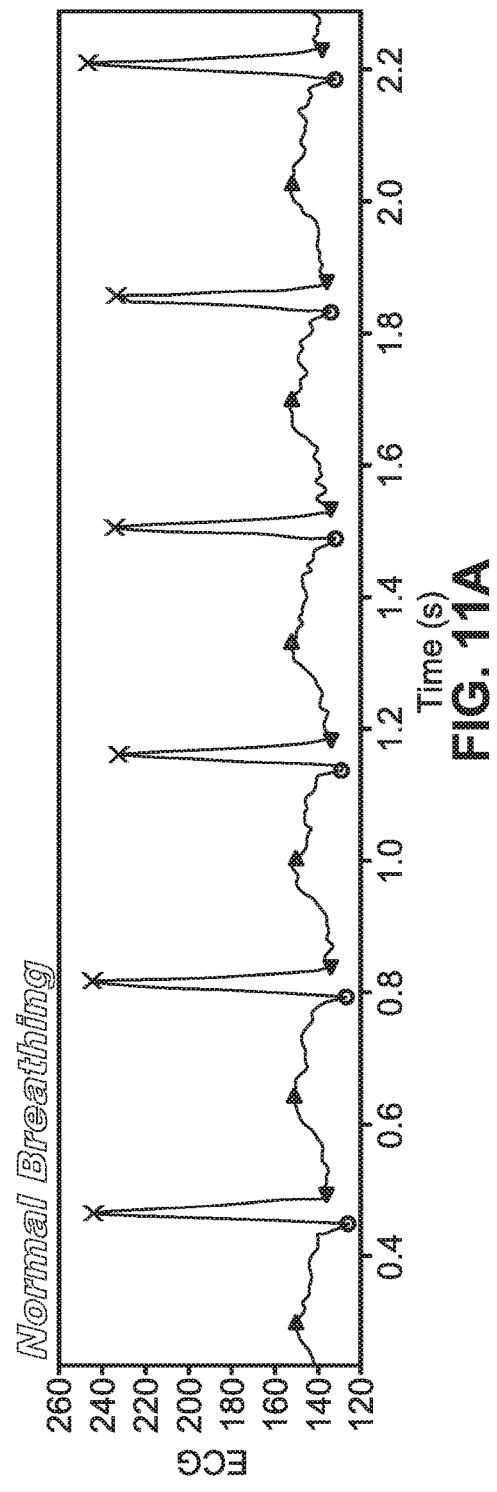
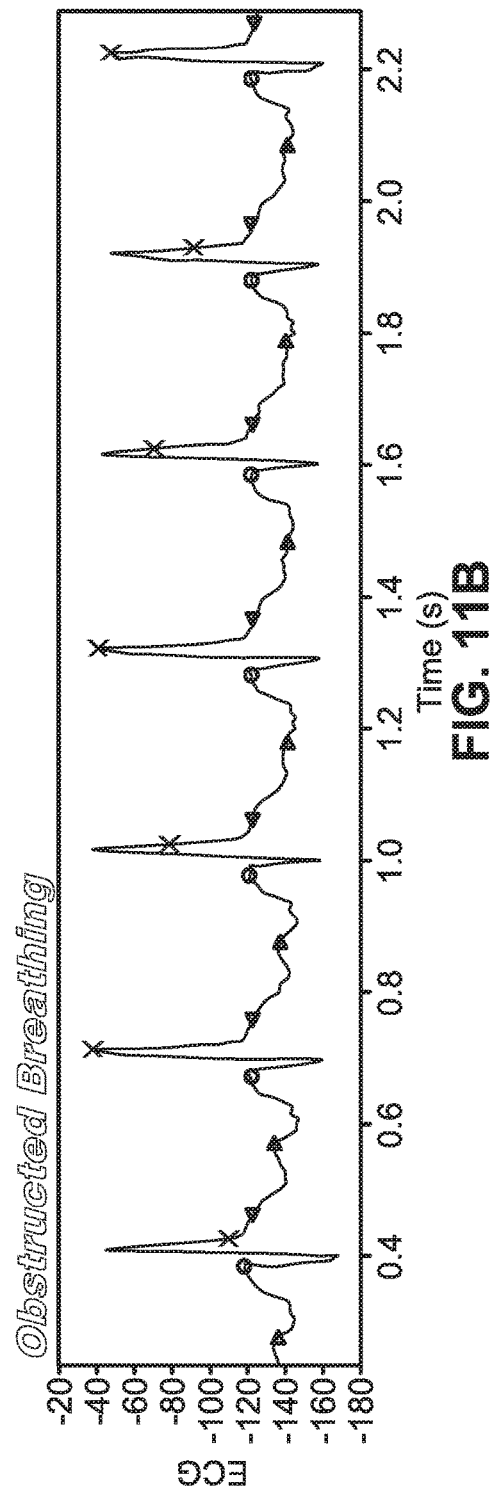
FIG. 11A
FIG. 11B

FIG. 15

| Feature name | Formula | Behavior |
|---|---|---|
| Instantaneous Breathing Rate | 60 / I+ E $_{total}$ | Increases during obstructed breathing |
| Classic I:E ratio | I / E $_{total}$ | Decreases during obstructed breathing |
| Active I:E ratio | I / ($E_A$ + $E_L$) | Decreases during obstructed breathing |
| Labored Exhalation Time | $E_L$ | Increases during obstructed breathing. Sometimes non-existent (zero) during normal breathing. |
| Passive Exhalation Time | $E_P$ | Decreases during obstructed breathing. Sometimes non-existent (zero) during obstructed breathing. |
| Inhalation time | I | Decreases during obstructed breathing |
| Active exhalation time | $E_A$ | Decreases during obstructed breathing |
| Upper respiratory slope | $m_{up}$ | Increases during obstructed breathing (less steep) |
| Lower respiratory slope | $m_{low}$ | Increases during obstructed breathing (less steep) |

FIG. 16

| Feature name | Formula | Behavior |
|---|---|---|
| Heart rate | ECG R-R interval | Increases during obstructed breathing |
| Heart rate variability | ECG R-R interval | Increases during obstructed breathing |
| P-wave shape and amplitude | ECG | Changes during obstructed breathing |
| T-wave shape and amplitude | ECG | Changes during obstructed breathing |
| S-wave shape and amplitude | ECG | Changes during obstructed breathing |

FIG. 17

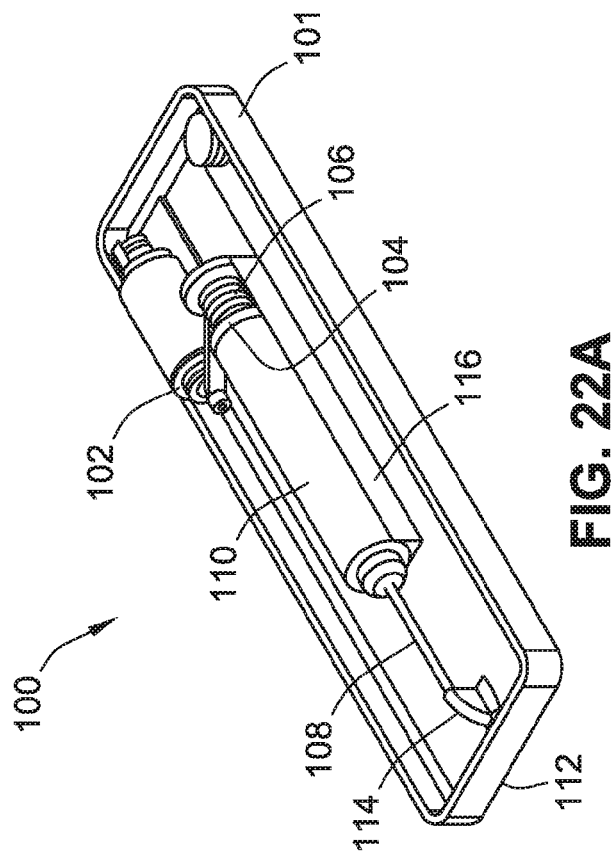
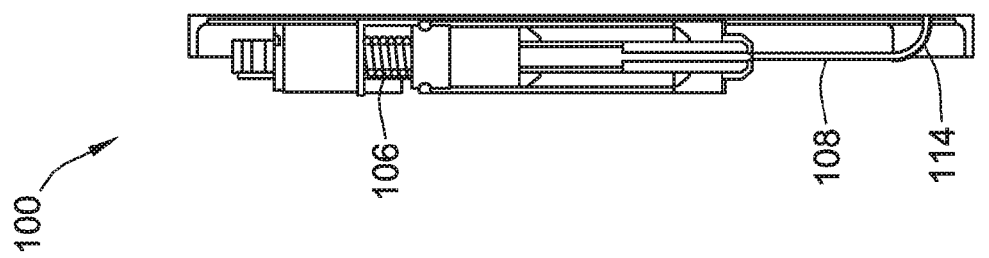

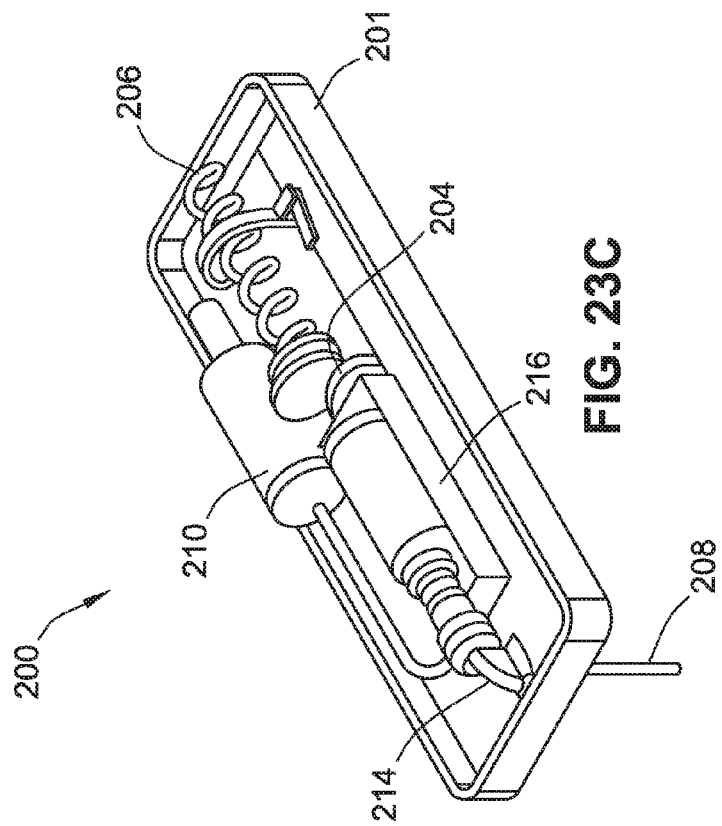
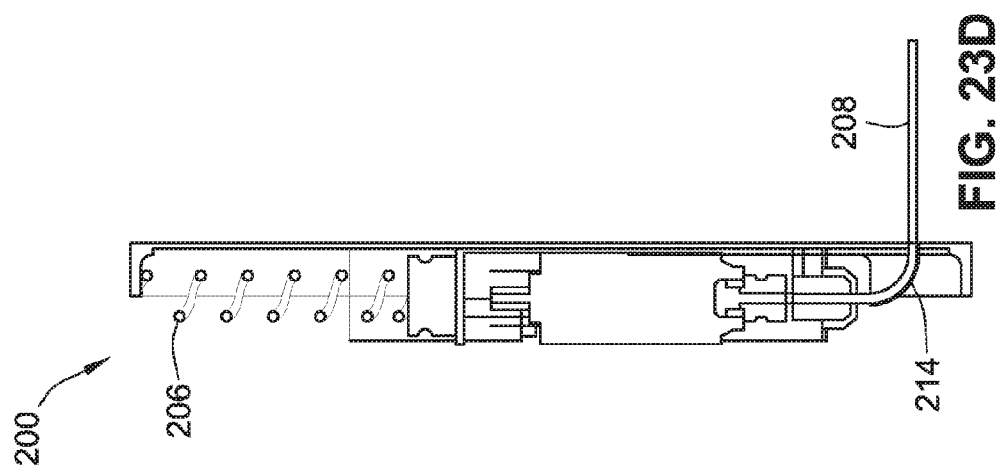

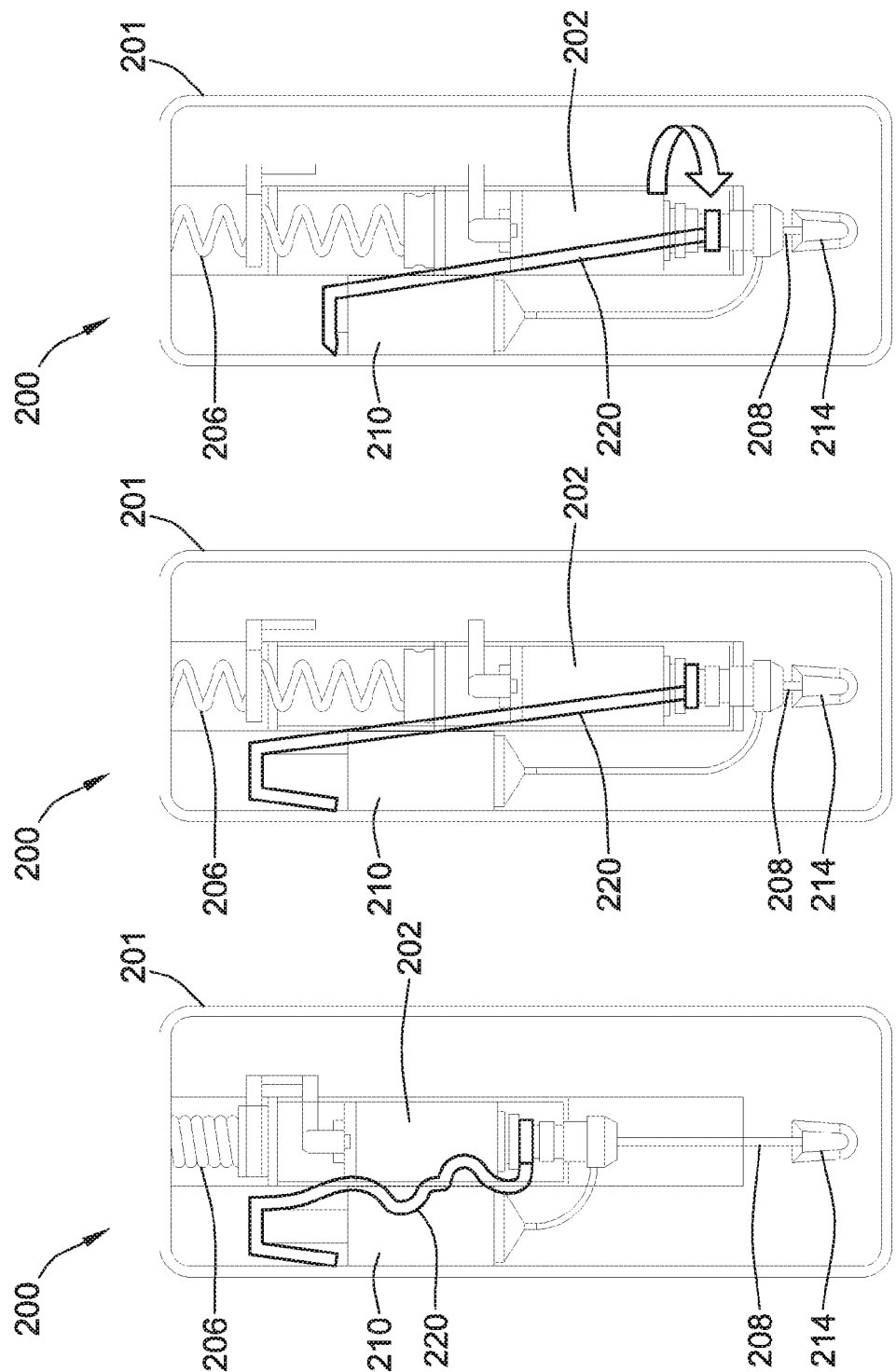

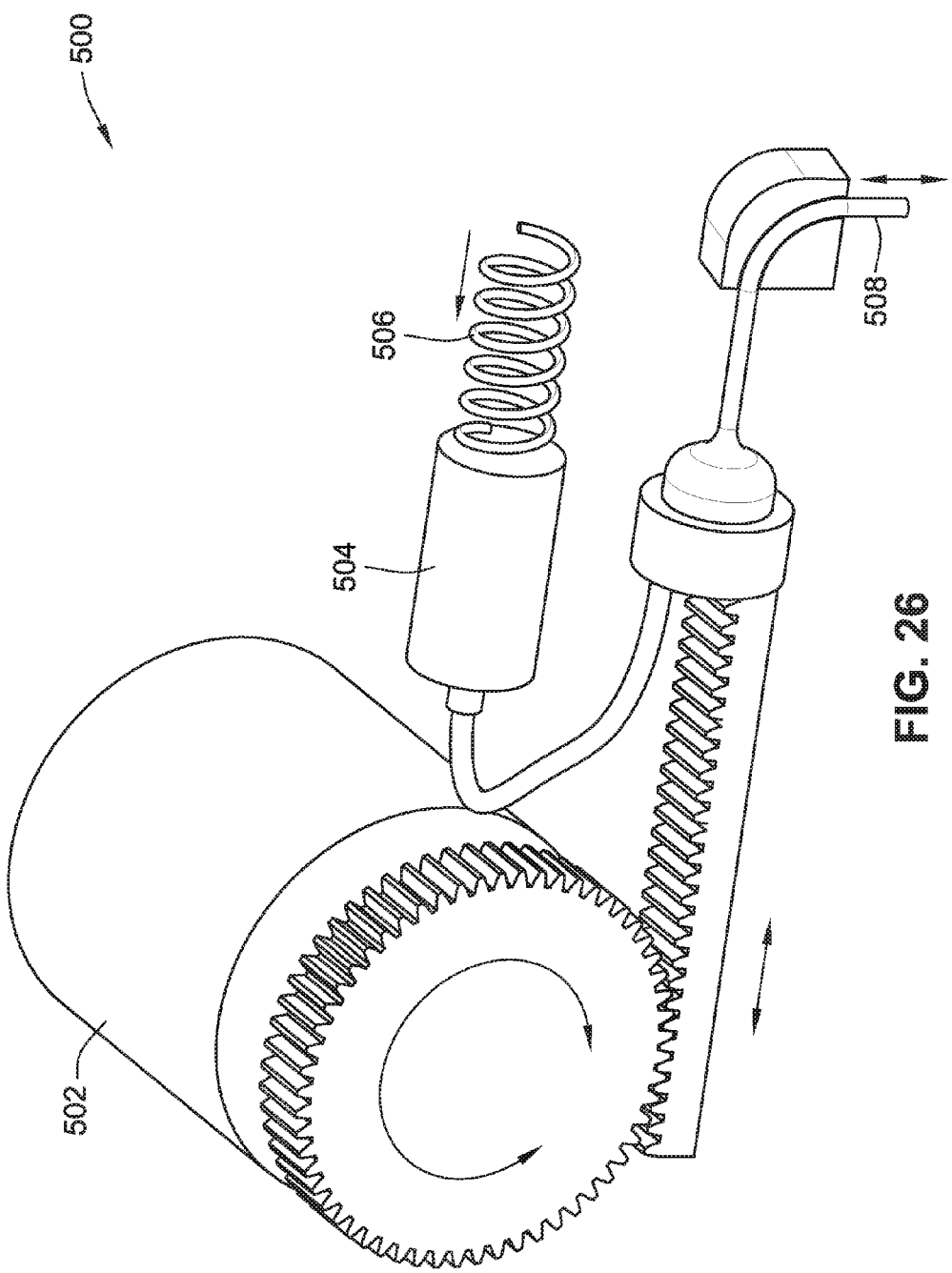

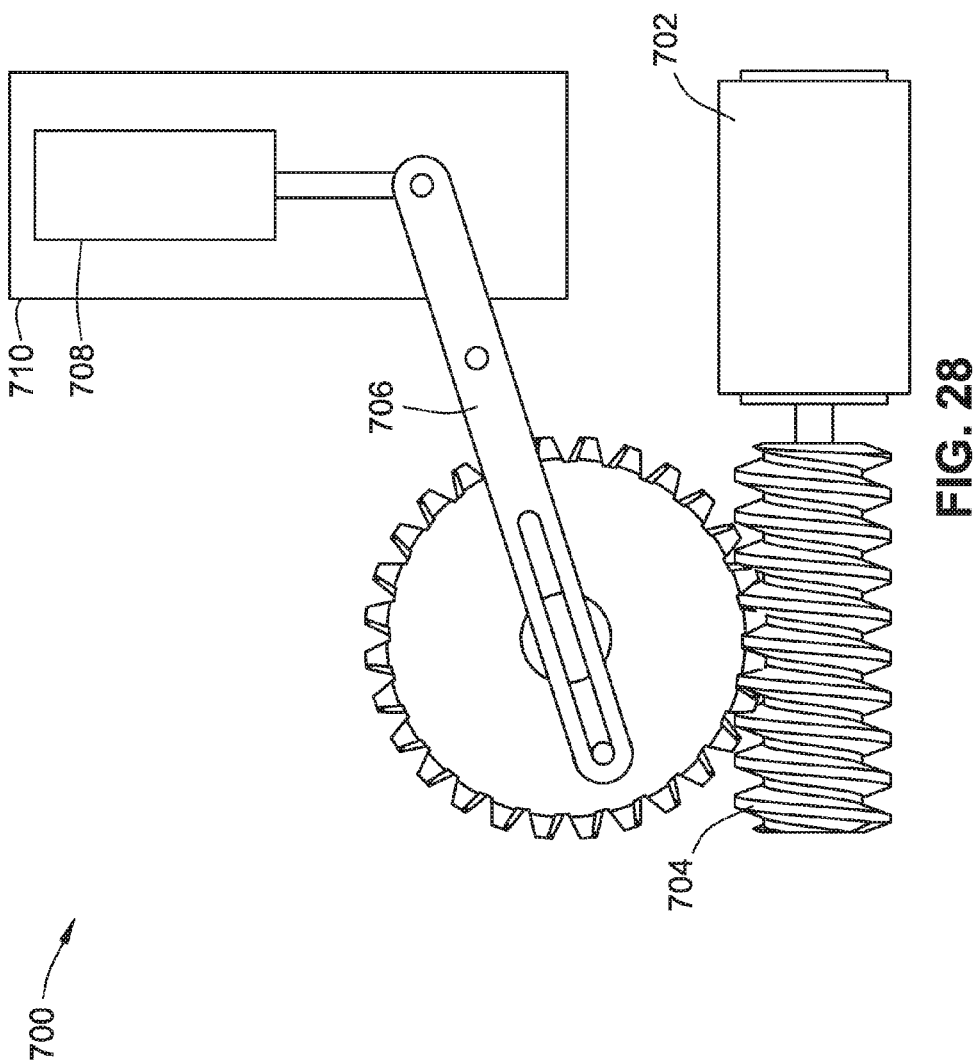

SYSTEMS AND METHODS FOR MONITORING, MANAGING, AND TREATING ASTHMA AND ANAPHYLAXIS

CROSS-REFERENCE TO RELATED APPLICATION

This application is a continuation of International Application Serial No. PCT/US2016/062920, filed Nov. 18, 2016, and titled "Systems And Methods For Monitoring, Managing, And Treating Asthma And Anaphylaxis," which claims priority to and benefit of U.S. Provisional Patent Application Ser. No. 62/257,190, filed Nov. 18, 2015, and titled "Systems And Methods For Monitoring, Managing, And Treating Asthma And Anaphylaxis," each of which is hereby incorporated by reference herein in its entirety.

FIELD OF THE INVENTION

The present invention relates to compact wearable devices for management and treatment of asthma or anaphylaxis and components to provide objective measures of allergic reactions.

BACKGROUND OF THE INVENTION

Asthma is a common chronic condition affecting children and adults and is characterized by inflammation of the lower respiratory tract, cough, breathlessness, and recurrent episodes of polyphonic (musical) expiratory wheezing. The inherent defect in asthma is of airway smooth muscle or the inflammatory milieu which renders the lower airway smooth muscles hyper-reactive. Asthma exacerbation is defined as a sudden worsening of asthma symptoms that can last days to weeks. Patients with asthma are prone to acute exacerbations secondary to a variety of triggers, including viral or bacterial infections, pollens, smoke, aeroallergens, mold, chemicals, and fluctuations in air temperature. Although mortality from asthma is decreasing worldwide, it remains one of the most common causes of death in both children and adults, and morbidity remains a significant problem. Generally, deaths from asthma exacerbation occur prior to or shortly after patients are seen by emergency medical personnel suggesting that the timing of when asthmatics seek medical attention profoundly determines outcome.

Currently, there are no commercially available technologies to monitor and analyze breathing in asthma that could provide patients warning of impending respiratory failure. Commercially available peak flow meters provide snapshots of pulmonary function, but are quite unreliable. Patients and their families generally recognize they are "unwell", and often initiate "sick" asthma care plans that include frequent inhalation of bronchodilator medicines, and occasionally initiation of enteral steroid therapy. Generally, these patients will contact their primary care physician in the acute phase, and seek advice as to whether and when they should be seen in the office, clinic, or emergency room. Commonly, patients receiving "sick" asthma care plan management improve at home and are not seen during the acute illness by a physician. However, it is not uncommon that patients who remain at home and who self-administer frequently inhaled bronchodilator therapy (more frequently than every 2-3 hours) for prolonged periods of time (>24 hours) abruptly (within minutes to hours) worsen prompting calls to 911 for emergency services in the home. A small percentage of these patients require resuscitation and die in the home or prior to arrival in the emergency room. An early warning signal instructing asthma patients to seek medical attention for advancing respiratory distress prior to them becoming critically ill would be of monumental importance in preventing asthma morbidity and mortality. In addition, detecting and treating asthma attacks early have important therapeutic value in that each asthma attack makes the underlying disease worse. Thus, a major challenge in pulmonary medicine is to design a technology enabling outpatient monitoring of asthma severity in real time. In addition to asthma, this technology is useful in diagnosing the progression of Chronic Obstructive Pulmonary Disease ("COPD"), which includes chronic bronchitis and emphysema.

Anaphylaxis, according to another example, is a severe and potentially life threatening allergic reaction to foods, insect venom, medications, and other allergens. The symptoms of anaphylaxis are numerous, complex and confusing. Many people do not recognize the early symptoms, including teachers and child caregivers, or choose to downplay or ignore the danger out of fear or denial. Denial is a common coping mechanism for stress, and may cause a person to delay or fail to react to the situation. Time is critical when experiencing anaphylaxis.

The only treatment for anaphylaxis is the injection of epinephrine. One in 50 Americans are at risk of experiencing anaphylaxis in their lifetime, with estimates of 500-1000 people dying from anaphylaxis every year.

After contact with an allergen, a person can have as little as 10 minutes (bee sting) to 30 minutes (food allergy) until cardiac arrest and death. Chances of survival increase the sooner they receive a dose of epinephrine, commonly applied using an EpiPen®, which can reverse life-threatening airway constriction. This is an especially difficult problem in children and their parents, and in many situations lives have been lost because epi-pens aren't available, can't be found, or have expired, or the sufferer has simply lost consciousness before they can inject themselves. Additionally, allergy testing is performed in physicians' offices by providing a small amount of allergen to the patient and asking the patient how they feel. There is no objective measure to provide the physician to either gauge the degree of allergic response or even its presence. Patients allergic to foods and drugs, such as penicillin and chemotherapy drugs, are treated by desensitizing them, giving the patients small amounts of allergen in increasing doses. Again, the only feedback to the physician is to ask the patient if they feel an allergic response. Thus, lives could be saved if it were possible to detect the early onset of anaphylaxis, and to initiate treatment automatically.

Accordingly, present embodiments are directed to solving the above and other needs, including providing technological components combined and configured into various different device embodiments for the treatment of acute conditions, such as anaphylaxis and asthma, as described herein.

SUMMARY OF THE INVENTION

According to one aspect of the present invention, a physiologic sensor module includes at least one wearable sensor that is configured for wearing on a human body part and for measuring at least one biological signal. The module further includes at least one controller communicatively coupled to the wearable sensor and configured to receive the biological signal from the wearable sensor. The controller is further configured to process the biological signal in real-time, extract one or more clinical features from the biological signal, and based on the clinical features, determine detection of respiratory failure or probability of future occurrence. Optionally, the biological signal includes biosensor data indicative of measured levels of an inflammatory mediator. Optionally, yet, the physiologic sensor module further includes a wearable injector of epinephrine or other therapeutic agent coupled to the at least one controller, the wearable injector being mounted to a human body part and including a movable needle, the needle delivering a bolus of the epinephrine or other therapeutic agent, in response to the detection of anaphylaxis, to treat anaphylaxis symptoms.

According to another aspect of the present invention, a medication injector module includes a wearable injector on a human body part, the wearable injector having an enclosure for housing a movable needle in a retracted position and a reservoir for storing epinephrine. The needle is movable at least in part outside the enclosure in an injecting position. The module further includes at least one controller communicatively coupled to the wearable injector and configured to receive a biological signal. The controller is also configured to process the biological signal in real-time, extract one or more clinical features from the biological signal, and based on the clinical features, determine presence of anaphylaxis symptoms. The controller is further configured to automatically cause the needle to move to the injecting position and deliver a bolus of the epinephrine to the human body part.

According to an alternative aspect of the present invention, a physiologic module is directed to detecting and treating symptoms of anaphylaxis. The physiologic module includes at least one wearable sensor for measuring at least one biological signal, and a wearable injector. The wearable injector has an enclosure for housing a movable needle in a retracted position, and a reservoir for storing epinephrine. The needle is movable at least in part outside the enclosure in an injecting position. The physiologic module further includes at least one controller communicatively coupled to the wearable sensor and to the wearable injector. The controller is configured to receive the biological signal from the wearable sensor, process the biological signal in real-time, and extract one or more clinical features from the biological signal. Based on the clinical features, the controller is further configured to determine the presence of an anaphylaxis symptom, and in response to the anaphylaxis symptom, automatically cause the needle to move to the injecting position and deliver a bolus of the epinephrine to a human body part.

According to another alternative aspect of the present invention, physiologic monitoring modules are directed to detecting early signs of anaphylaxis, COPD, and/or asthma, and to present associated data to a physician.

According to another alternative aspect of the present invention, a sensor module includes a histamine sensor configured for measuring a histamine level of a patient, the histamine sensor outputting a signal indicative of the measured histamine level. The sensor module further includes at least one controller communicatively coupled to the histamine sensor and configured to receive the signal from histamine sensor, process the signal in real-time, extract one or more clinical features from the signal, and based on the clinical features, determine detection of an allergic reaction.

According to another alternative aspect of the present invention, a manual injector module includes a wearable injector having an enclosure for housing a movable needle in a retracted position and a reservoir for storing a therapeutic agent. The needle is movable at least in part outside the enclosure to an injecting position. The manual injector module further includes a manual activator coupled to the injector and configured to, upon activation, cause the needle to move to the injecting position.

According to another alternative aspect of the present invention, a method is directed to detecting and treating symptoms of anaphylaxis, the method including sensing data via one or more non-invasive sensors, and sending the data to a controller configured to with an anaphylaxis detection algorithm. Based on the data, and in response to the controller causing the anaphylaxis detection algorithm to determine a high likelihood of anaphylaxis, triggering a biosensor is triggered to take a biological sample, and, in response to the biosensor confirming that anaphylaxis is occurring, a needle is triggered to insert an auto-injection of epinephrine.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 11A is a plot showing electrocardiogram ("ECG") features for normal breathing.

FIG. 11B is a plot showing ECG features for obstructed breathing.

FIG. 15 is a diagram showing a classical machine learning pipeline for the AOS algorithm of FIG. 13.

FIG. 16 is a table showing physiologic features of a respiration signal.

FIG. 17 is a table showing features of an ECG & plethysmograph ("PLETH") signal.

FIG. 22A is a perspective view of a smart auto-injector in a pre-operation position, according to one embodiment.

FIG. 22B is a side view of the smart auto-injector of FIG. 22A.

FIG. 23C is a perspective view of the smart auto-injector of FIG. 23A in a post-operation position.

FIG. 23D is a side view of the smart auto-injector of FIG. 23C in the post-operation position.

FIG. 23E is a side view of the smart auto-injector of FIG. 23A in an initial state.

FIG. 23F is a side view of the smart auto-injector of FIG. 23A in a needle insertion state.

FIG. 23G is a side view of the smart auto-injector of FIG. 23A in a medication injection state.

FIG. 26 is a perspective illustration showing a rack-and-pinion drive for a smart auto-injector, according to another alternative embodiment.

FIG. 28 is a side illustration of a worm-gear mechanism for a smart auto-injector, according to another alternative embodiment.

Figure 1:
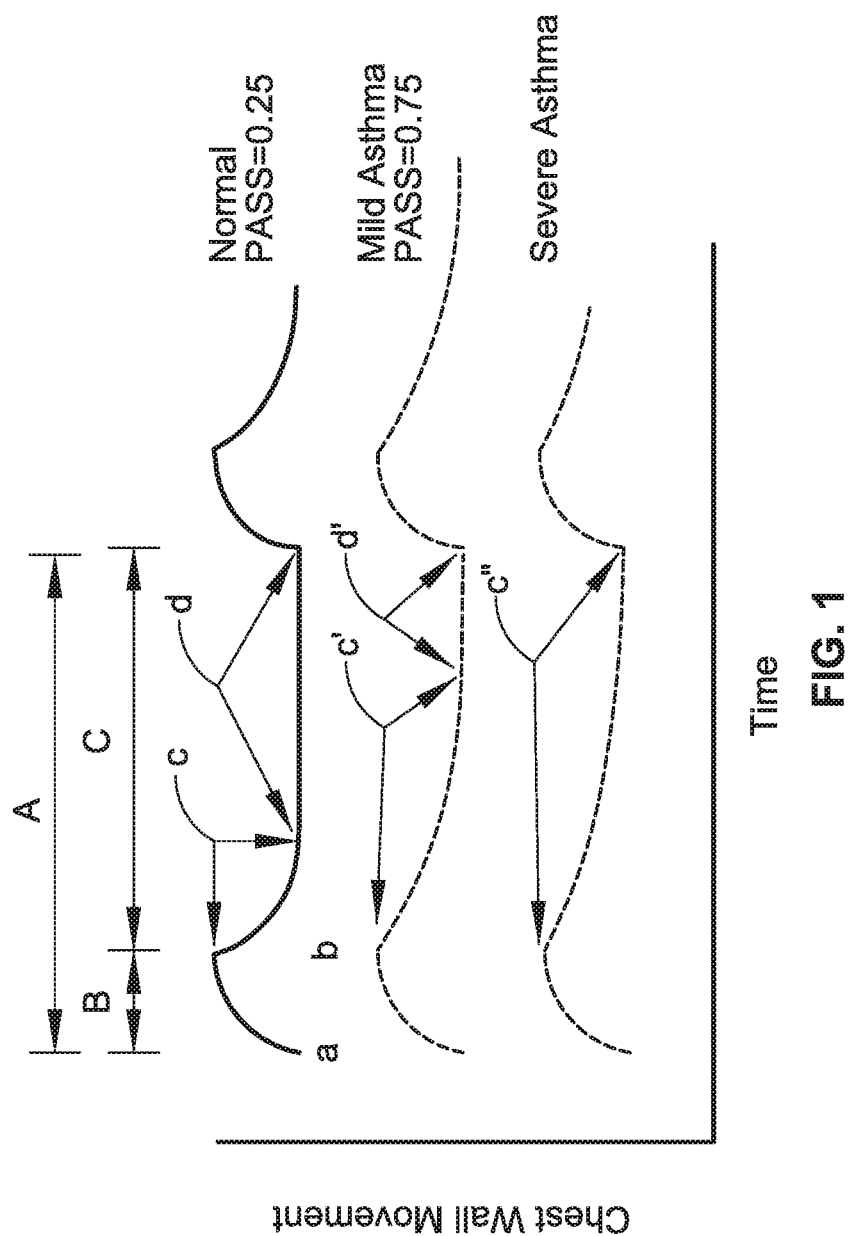
FIG. 1 is a plot illustrating respiration signals indicative of chest wall movement over time under different levels of obstructed breathing.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Various unique and novel technologies are currently being developed at the Wyss Institute, in collaboration with Boston Children's Hospital and UMASS Medical School. These technologies are being developed and integrated into medical devices for the management and treatment of asthma and anaphylaxis. Each of the underlying technological components is described separately, based on respective unique and novel features. These technological components can be combined and configured into various different device embodiments for the treatment of acute conditions, such as anaphylaxis and/or asthma conditions.

Generally, the description below describes a sensor module that is configured to detect various acute conditions, including asthma and anaphylaxis. According to one example, the sensor module includes a wearable device that monitors breathing, assesses asthma severity, and alerts to dangerous changes. According to another example, the sensor module includes a wearable device that alerts upon early detection of anaphylaxis, auto-injects epinephrine, and calls emergency services (e.g., initiates 911 call) and/or family. According to yet another example, the sensor module includes one or more monitors for use in a hospital or a physician's office to provide objective measures of a patient's physiologic response to an allergen.

Symptom Detection, Alarming, and Auto-Injection Device

Generally, an auto-injection device is described below in reference to the detection of, but not limited to, asthma and anaphylaxis. The auto-injection device detects and/or provides an alarm when detecting symptoms of such acute conditions as asthma and/or anaphylaxis. For example, the device is a non-invasive, wearable device that senses chest wall movement and analyses user breathing pattern and asthma severity in real time, and alerts the user (or guardian) of critical asthma severity.

According to one aspect of the present disclosure, a non-invasive wearable device is directed to monitoring and alarming for changes in asthma severity. The system is comprised of a non-invasive breathing sensor that gathers physiologic signals from the user's body, and extracts a set of features relevant to the user's respiration. It then passes these variables into a novel algorithm in order to calculate a unique indicator of asthma severity, called the Airway Obstruction Severity Score ("AOS"). The software alarms when the calculated severity significantly deviates from historical or patient normal values. The device will be effective even in patients with rapid onset and worsening of bronchospasm who are alone or who lose consciousness before being able to call for help.

An algorithm is based on a machine learning framework and will consider different features from the respiration signals, such as the Inspiration Time (i) to Expiration time ratio (e) ratio, or i:e ratio, to assess the severity of bronchoconstriction, which is one of the most significant symptoms of anaphylaxis. This risk is the AOS, and the algorithm is referred to as the AOS algorithm (described in more detail below in the respective section of the disclosure). By way of example, the device operates to alert a user that their breathing has reached a certain severity threshold in accordance with the following exemplary device operation for detecting asthma severity:
  A. Sensing chest wall movement of a subject using a non-invasive device with a breathing sensor,
  B. Determining measures representative of active exhalation time and total exhalation time for each breath using the sensed physiologic signal, and
  C. Generating an indication of asthma severity using AOS according to the respiratory measures generated from the sensed physiologic signal.

The device may consist of a wearable breathing sensor placed on the subject's chest, and a processor attached to or embedded within it, or housed externally within a smartphone, smartwatch or other device. In other embodiments, the wearable device may perform all of the operations (sensing, data acquisition & algorithm execution) and use a smartphone or smartwatch only as a method to alert the user.

According to one example, a method of operating a device to detect asthma severity includes having a physiologic signal (e.g., chest wall movement) sensed using a respiration sensor. The physiologic signal provides surrogate information of respiration of the subject. Values of active exhalation time and total exhalation time for each subject breath are then calculated on the mobile device using the sensed physiologic signal, and fed into the AOS algorithm. An indication of asthma severity, or AOS, of the subject is generated according to the features extracted from the breathing data, including an awareness of historical trends and likelihood of getting worse or improving, possibly with machine learning approaches. If an AOS threshold is exceeded, an alert is sent to the user on the mobile device.

The dynamic features as well as statistical features are incorporated in a machine learning framework tailored specifically to an individual subject, which is then employed to assess the pathological fluctuations in the breathing signal related to the risk of bronchoconstriction. The assessed risk score from the algorithm is compared to the clinician rating risk score of asthma (such as the first study described below).

Onset of an anaphylactic event is marked by several physiologic signals. The present disclosure is directed to a wearable sensor providing these data points. By taking these variables into account, accurate prediction of an anaphylactic event is performed.

Furthermore, the present disclosure also describes an integrated wearable device that detects the early onset of anaphylaxis and, then, automatically injects epinephrine. Using sensors on or inside the body, the wearable device carefully monitors the biology and physiology of the wearer, in possible combination with location or environmental measurements, and activates an alarm when the early stages of anaphylaxis are detected. If required, the device automatically injects epinephrine and potentially notifies emergency services (e.g., dialing 911) or family members.

The present disclosure further describes a wearable device and system that monitors the wearer's physiology and detects the early onset of anaphylaxis. In the event of detection, the system alerts the user and, if needed, auto-inject epinephrine. The system includes non-invasive and/or indwelling biosensors that stream data to a processor, which runs software that processes the data in real time and executes an anaphylaxis detection algorithm, as well as a wearable auto-injector including a needle and syringe containing a dose of epinephrine.

Anaphylaxis causes a systemic reaction, which may present in a variety of symptoms. Because of this, other types of physiologic sensors are optionally incorporated into the system in addition to a breathing sensor. For example heart rate, blood pressure, galvanic skin response (GSR) and/or skin temperature sensors are optionally used. Based on their relevance to a diagnosis of anaphylaxis, these sensors allow the disclosed AOS algorithm to more accurately detect the onset of an anaphylactic event.

Accordingly, the AOS algorithm is based on a machine learning framework and considers these features, taking into account historical trends, to assess the severity of anaphylaxis. If a threshold is exceeded, an alert is sent to the user on their mobile device and epinephrine is automatically injected by the device. The device optionally alerts emergency services, family, or caregivers automatically upon injection of epinephrine.

According to a specific example, a method operates a device to detect anaphylaxis onset. The physiologic signals are measured using wearable sensors on the body, or using indwelling chemical biosensors within the body. The physiologic signals are related, for example, to one or more of breathing data, ECG data, BP data, skin temperature, microphone data, GSR data, and biosensor data. Specific features of the user's physiologic status are then extracted from these raw signals and fed into an anaphylaxis detection algorithm (e.g., the AOS algorithm). If detected, the user is alerted to the anaphylactic episode and epinephrine is auto-injected, if needed.

Wearable Physiologic Sensors

Wearable physiologic sensors are directed to the detection of, but are not limited to, asthma and anaphylaxis. Two exemplary sensory modes utilize one or more non-invasive physiologic sensors to generate the signals used for feeding into the detection algorithms. For an asthma detection sensory mode, reliance is optionally based solely on respiration signals. However, for an anaphylaxis sensory mode, additional sensors are used, such as:
  ECG,
  blood pressure,
  skin temperature,
  skin conductance, pulse oximeter,
microphones, and/or
biosensors for histamine and other chemical markers of allergic response.

These sensors are optionally off-the-shelf physiologic sensors. For respiration sensing, various sensing methods are used, such as a) impedance pneumography, a common way to electrically measure respiration using electrodes placed on the chest;
b) respiratory inductance plethysmography (RIP), a system where belts or straps are placed around the subject's chest in order to measure the expansion and contraction of the thorax;
c) flexible soft-sensors that can be placed in straps around the chest to monitor chest wall expansion, similar to RIP belts but more elastic and less restrictive);
d) ECG Derived Respiration (EDR) (respiration waveform acquired using signals from ECG skin leads);
e) nasal thermistors or thermocouples (respiration waveforms acquired by measuring changes in nostril air temperature); and/or
f) proximity sensors on anterior/posterior chest that measure thorax expansion, and
g) g) acoustic sensors that measure breathing sounds.

According to one benefit of the described devices, a capability of "two-step" authentication of anaphylaxis is provided, as follows: the first step is to confirm anaphylaxis using non-invasive physiologic sensors. If this test is passed, a biosensor will take a biological sample to confirm that anaphylaxis is occurring. This two-step authentication ensures that wearers are never injected with epinephrine based on a false alarm. Alternatively, the patient is monitored continuously for levels of biomarkers such as histamine.

According to another benefit, one or more of the described devices use Wyss Institute-developed "soft sensors" for respiration sensing and biosensors for histamine sensing.

Airway Obstruction Severity Score ("AOS") Algorithm

The AOS algorithm is directed to using an incoming continuous respiration waveform to calculate the severity of asthmatic breathing, i.e., on a percentage scale of 0 to 1 where 0=healthy and 1=severe asthma attack. The algorithm is based on a machine learning framework and considers different features from the respiration signals to assess the severity of bronchoconstriction, as well as historical data for the person wearing the device. The dynamic features, such as amplitude and frequency fluctuations, are derived from the breathing signal using a time-frequency decomposition either using wavelet based decomposition or empirical model decomposition. The statistical features, such as instantaneous mean and instantaneous variances, are derived from the breathing signal using a point process modeling approach. The dynamic features as well as statistical features are incorporated in a machine learning framework tailored specifically to an individual subject, which is then employed to assess the pathological fluctuations in the breathing signal related to the risk of bronchoconstriction. This risk is the AOS.

In reference to FIG. 1, patients with asthma exacerbation experience expiratory flow limitation leading to a prolonged exhalation phase of breathing. Breathing symptoms include wheezing (change in ratio of inspiration to expiration), change in breathing rate (breaths/minutes), and/or breathing becomes more regular as it becomes more difficult to do so (e.g., the person will generally stop eating or speaking to concentrate on breathing). Cardiac symptoms include a sudden change in heart rate, which usually is presented as bradycardia (slower heart rate), or, sometimes, as tachycardia (faster heart rate). Other cardiac symptoms include dysrhythmia, or unpredictability in inter-beat interval, or a sudden decrease in blood pressure (hypotension). In addition, other symptoms that are often reported, but that can vary greatly between individuals (and some can be difficult to accurately quantify) include flushing (increased skin temperature), itchiness of the throat, or difficulty in swallowing.

Historically, the inspiratory to expiratory (I:E) time ratio (where the inspiratory and expiratory times refer to the periods during which a subject inhales ("B" in FIG. 1) and exhales ("C" in FIG. 1), respectively, has been used in the past as a single component of clinical asthma severity scores to roughly gauge asthma severity of patients seen in emergency rooms and hospital wards. During an asthma exacerbation, as bronchoconstriction worsens, the i:e ratio reduces (expiration prolongs relative to inspiration) due to difficulty exhaling.

However, during normal breathing at low resting rates, the i:e ratio may also appear equally short as to that seen in asthma (see dashed line). Physicians recognize worsening asthma clinically when a reduced i:e ratio is accompanied by difficulty exhaling and respiratory distress along with a history suggestive of asthma exacerbation. Therefore, technologies to measure i:e ratio alone cannot be reliably used to estimate asthma severity. Asthma severity is accurately and sensitively scored by measuring and calculating the ratio of the active component of exhalation (when airflow out of the lungs is above zero) as a function of the entire expiration phase of breathing.

According to one aspect of the AOS algorithm, a method is directed to calculating asthma severity in real-time, from breath-to-breath, and averaged over time. According to another aspect of the AOS algorithm, a method is directed to calculating i:e ratio (in contrast to current methods), which better reflects the real severity of breathing. According to another aspect of the AOS algorithm, a feature is directed to the ability to predict the onset of an asthmatic episode even before breathing severity worsens.

An anaphylaxis detection algorithm expands upon the AOS algorithm described above, to detect the early onset of anaphylaxis. Inputs to the algorithm include the respiration signal, and also a collection of other physiologic signals gathered from wearable non-invasive sensors, such as:
ECG,
blood pressure,
skin temperature,
skin conductance,
pulse oximeter,
microphones, and/or
Global Positioning System ("GPS") (to determine, for example, if the patient is running or is stationary).

In addition, this algorithm optionally uses input from biosensors (described in the following section) that acquire signals from biological samples. These signals are fed into the machine learning algorithm. This algorithm considers different features from the input signals to assess the likelihood of an imminent anaphylactic attack. The dynamic features of the signals, as well as statistical features, are incorporated in a machine learning framework tailored specifically to an individual subject, which is then employed to assess the pathological fluctuations in the signals related to the risk of anaphylaxis.

According to one aspect of the anaphylaxis algorithm, a feature is directed to the ability to detect the early onset of anaphylaxis.

Biosensors For Symptom Detection

Biosensors are directed to detecting, but are not limited to, asthma and anaphylaxis. By way of example, a biosensor detects the early stages of anaphylaxis by measuring levels and rates of change of levels of physiological mediators of anaphylaxis, such as histamine, tryptase, and platelet activation factor, in interstitial fluids, blood, or other biological samples (e.g., saliva, tears).

An allergic reaction is often triggered by an uncontrolled production of IgE antibody followed by the release of histamine. Detecting sudden changes in histamine levels of blood are potentially good indicators of a life threatening allergic reaction. An electrochemical histamine biosensor for use in detecting the sudden changes in histamine levels is based on current glucose monitors used in diabetes monitoring. A proof of concept sensor based on the enzyme diamine oxidase has been demonstrated. The anaphylaxis detector leverages glucose monitor designs and utilizes an indwelling sensor or an injectable sensor that is inserted on demand or when non-invasive sensors (e.g., physiologic monitors described above) detect the potential for development of an allergic reaction.

Detection of a high level or a rapid rise in histamine serves as a measure of early anaphylaxis to warn a physician or patient of the existence of an allergic reaction, or to trigger actuation of an epinephrine auto-injector. Histamine sensors require access to blood or interstitial fluids. This is achieved in several ways, by way of example. For physician use, a sensor electrode is placed under the skin with a needle. For periodic measurements, blood is taken from the patient and applied to the sensor. Access to subcutaneous fluid is also obtained with micro-needle patches, e.g., small needles penetrate the skin. Each needle is connected to an electrode to gain sufficient signals.

Another subcutaneous access device is directed to burning small holes through the epidermis. In this device, interstitial fluid, then, leaks into small chambers in which detection electrodes are located. Numerous cells are optionally placed on a patch such that serial measurements are performed over time as each cell is energized.

Miniaturized Wearable Auto-Injector

In accordance with some aspects of the present disclosure, the sensor module includes a miniaturized wearable auto-injector that is directed to the injection of, but not limited to, epinephrine. In contrast to present-use injectors, and according to some aspects of the present disclosure, compact and miniaturized wearable injectors are stand-alone, manually activated, or configured to communicate with a central processor and wearable sensors. According to one exemplary aspect, the injectors of the present disclosure allow the user to attach the device to multiple sites on the body, such as the thigh, stomach, lower back, or upper arm.

In further contrast to some of the present-use injectors that are manually administered auto-injectors for injecting the drug intramuscularly, the injectors of the present disclosure are capable of injecting the drug either intramuscularly or subcutaneously depending on the physiology of the wearer, the need of the patient, and the drug being injected. Using a detection algorithm (such as one or more of the algorithms described above), a system in accordance with the present disclosure automatically injects epinephrine with varying dose options if the system detects the onset of anaphylaxis. If the onset of anaphylaxis continues, a second dose is injected automatically. The device may have disposable medication cartridges that are optionally replaceable, thereby making the device reusable. In addition, the device is capable of informing the users of battery status, and the expiration status of the medication, through a user interface or through communication with a smartphone.

According to some aspects of the present disclosure, a device is wearable on the body of a person and includes one or more of the following features:
- device is always present,
- device is discreetly hidden under clothes,
- device includes adjustable sizes for different body shapes,
- device is suitable to multiple sites on body, and/or
- device consists of hypoallergenic materials.

According to some aspects of the present disclosure, a device is wearable on the body of a person and includes one or more of the following features:
- a needle, made of upper-elastic materials, such as nitinol,
- capability of trigger manually, as a back-up or safety feature,
- disposable cartridges,
- multiple doses (0.15 milliliters, 0.3 milliliters, 0.5 milliliters, etc.),
- capability of multiple injections, based on duration anaphylactic episode,
- injection is either intramuscularly or subcutaneously,
- period expiration feedback is provided to the user by light-emitting diode (LED) indicator and/or audio indicator,
- miniaturized configuration, including, for example, micro-actuators, such as mechanical actuators (e.g., springs, pistons, jets, etc.), electromechanical actuators (soft actuators, piezo-actuators, micro motors, solenoids, etc.), and/or custom actuator,
- replaceable cartridges,
- integrated sensors to inject without any user interaction, and/or
- integrated with smartphone to notify emergency services (e.g., 911), family, and/or friends when injection occurs.

Figure 2A:
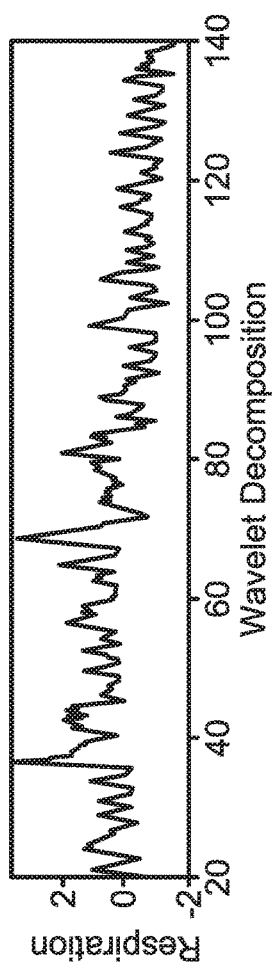
FIG. 2A is a plot showing raw respiratory data for time frequency decomposition of a breathing signal.
Figure 2B:
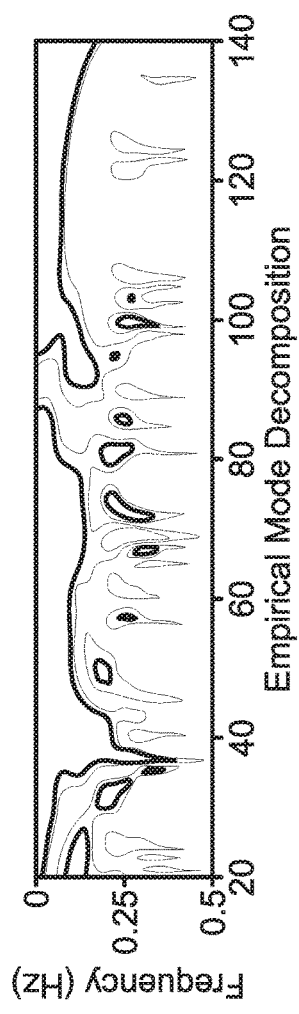
FIG. 2B is a plot showing wavelet-based decomposition for the time frequency decomposition of FIG. 2A.
Figure 2C:
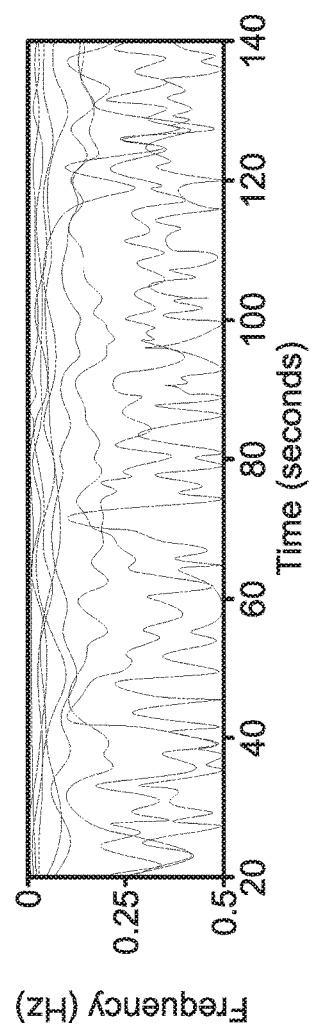
FIG. 2C is a plot showing an empirical model decomposition for the time frequency decomposition of FIG. 2A.

Referring to FIGS. 2A-2C, the algorithm includes different features that are based on respiration signals to assess the severity of bronchoconstriction. The dynamic features, such as amplitude and frequency fluctuations, are derived from the breathing signal using a time-frequency decomposition either using wavelet based decomposition or empirical model decomposition. The statistical features such as instantaneous mean and instantaneous variances will be derived from the breathing signal using a point process modeling approach.

Figure 3A:
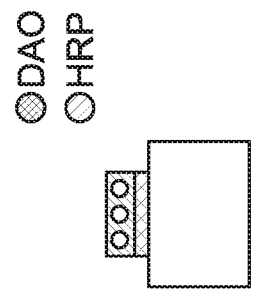
FIG. 3A is a schematic representation of Vinyl-SAM addition in a copolymerization process.
Figure 3B:
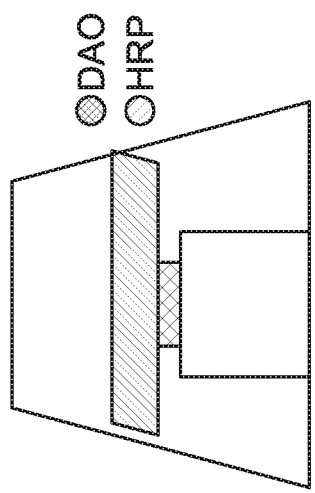
FIG. 3B is a schematic representation of drop addition of HRP+DAO+Fc+PEGDA monomer+AIBN, in the copolymerization process of FIG. 3A.
Figure 3C:
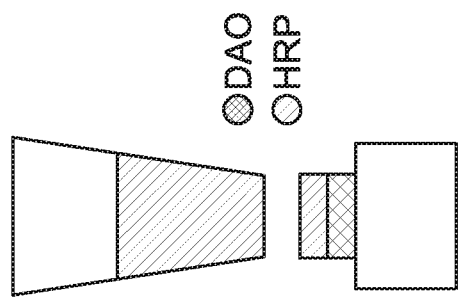
FIG. 3C is a schematic representation of addition of coverslip with Teflon™ monolayer and UV light exposure for 5 minutes, in the copolymerization process of FIG. 3A.
Figure 3D:
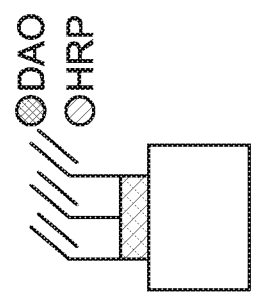
FIG. 3D is a schematic representation of immersing in DMSO to remove coverslip, in the copolymerization process of FIG. 4A.

Referring to FIGS. 3A-3D, a copolymerization method includes addition of Vinyl-SAM to the electrode surface (FIG. 3A) and a drop addition of HRP+DAO+Fc+PEGDA monomer+AIBN (FIG. 3B). The method further includes the addition of a coverslip with Teflon monolayer and UV light exposure for five minutes (FIG. 3C), and the immersing in DMSO to remove the coverslip and non-polymerized monomers (FIG. 3D).

More specifically, the copolymerization method is directed to a sensor modification process, in which the first step (FIG. 3A) chemically modifies the electrode to introduce a variety of functional groups that are known to participate in the polymerization process. The modification provides a robust immobilization of the subsequent polymer layer at the electrode surface.

In a second step (FIG. 3C), a mixture of enzyme, monomers, electroactive moiety, and a polymerization initiator is deposited onto the electrode surface. In a third step (FIG.

3C), the deposited mixture is spread over the electrode surface using a photomask to define the patterns to be polymerized. The assembly is further exposed to UV light to imitate polymerization. In a final step (FIG. 3D), the polymerization is stopped, the photomask removed, and the polymerized surface is washed to remove any non-polymerized and weakly-bound material.

Figure 4:
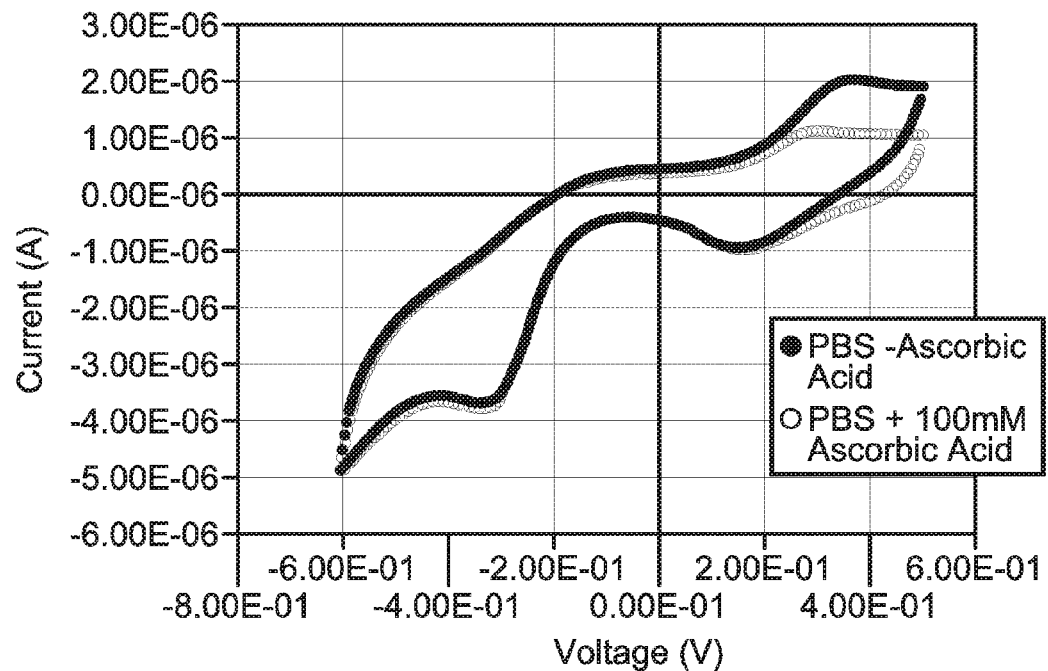
FIG. 4 is a plot showing interferences of ascorbic acid.

Referring to FIG. 4, a plot shows interferences of ascorbic acid, with ascorbic acid strongly interfering electrochemistry at positive detection potentials of greater than 0.2 Volts. A −0.36 Volt detection potential shows no interference from ascorbic/uric acid that is normally present in blood. The plot includes a curve for PBS-no ascorbic acid (i.e., absence of ascorbic acid) and a curve for PBS+100 mM ascorbic acid (i.e., presence of ascorbic acid).

More specifically, the plot of FIG. 4 demonstrates that the sensor is not sensitive to electroactive interferents, such as ascorbic acid or uric acid, which are commonly known as the main electrochemical interferents present in biological samples. The curve representing PBS +100 mM ascorbic acid represents the current measure at the electrode surface while applying an increasing potential. Passed 0.2 Volts, the presence of ascorbic acid is apparent. However, below 0.2 Volts, there is no difference between the presence or absence of ascorbic acid. The sensor operates below the potential threshold and is insensitive to this type of electrochemical interferents.

According to one embodiment, the sensor is a physiology sensor that uses or modifies an off-the-shelf sensor to generate respiratory waveform capturing chest wall movement. The sensor, according to another embodiment, is an anaphylaxis continuous biosensor that detects one or more of tryptase, histamine, IgE, and a platelet activating factor (PAF).

Figure 5:
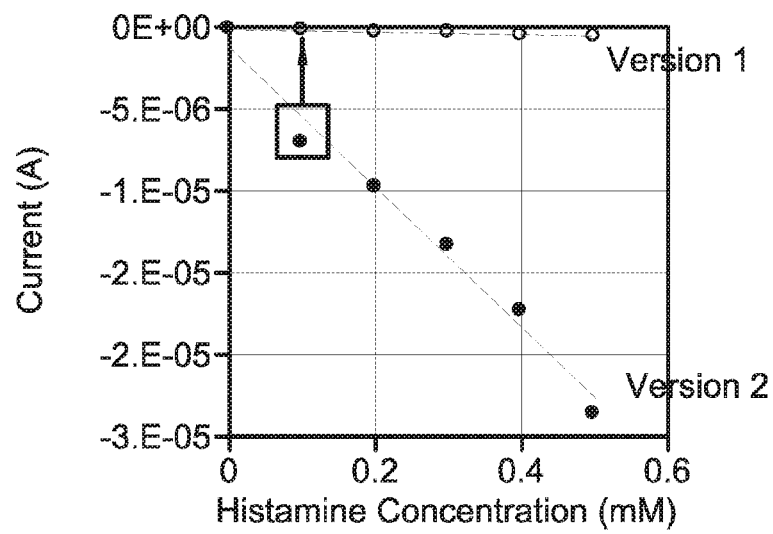
FIG. 5 is a plot showing sensor sensitivity increased ~100-fold.

Referring to FIG. 5, a plot shows a sensor sensitivity that is increased approximately 100 times over two versions, 1 and 2. The target sensitivities, for example, are 10 nM.

Figure 6A:
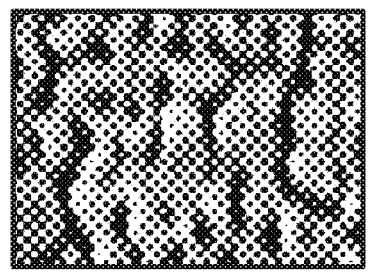
FIG. 6A is an image showing a Gold-Silver alloy co-deposited on a plain gold substrate.
Figure 6B:
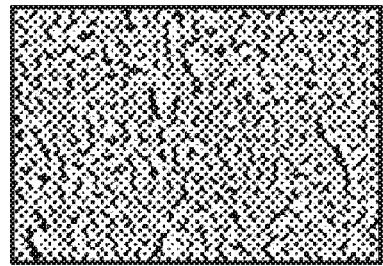
FIG. 6B is an image showing the sample of FIG. 6A after complete removal of silver (i.e., de-alloying).
Figure 6C:
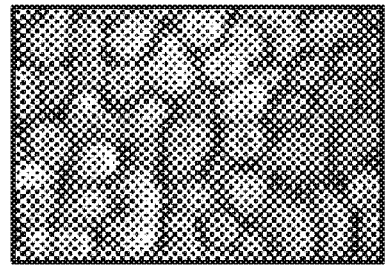
FIG. 6C is an enlarged view of FIG. 6B.

Referring generally to FIGS. 6A-6C, a method and device is directed specifically to the sensitive electrochemical detection of histamine in biological fluids. In accordance with one aspect of this method and device, an electrode is modified with an enzyme specific to histamine by entrapment in an electroactive polymer.

More specifically, an electroactive polymer is prepared in situ, i.e., a mixture of monomers and enzyme are deposited together onto the electrode and exposed to a UV light to initiate polymerization. The electroactive polymer is optionally prepared prior to deposition, mixed with the enzyme, and finally deposited onto the electrodes. The electroactive polymer is then left to dry in controlled atmosphere to cure.

The electroactive polymer allows the wiring of the enzyme core directly to the electrode. In doing so, the detection potential required to test the enzyme is considerably lowered, which allows keeping background signals from potential interferents low. Known electrochemical interferents are, for example, ascorbic acid and uric acid, both typically found in large concentration in biological samples.

To improve sensitivity, the electrode is nanostructured. Silver and gold are co-deposited during fabrication of the device. Upon immersion in nitric acid, the silver will dissolve, leaving nanometer-size cavities. The resulting nanostructured electrode possess a much higher surface area, as illustrated in FIGS. 6A-6C.

Gold-Silver alloy is electrochemically deposited onto a plain gold electrode or co-sputtered on a plain gold substrate. The surface area of the resulting electrode is, then, electrochemically assessed. According to one example, the area of a plain electrode is improved by a factor of 10, based on introducing nanoporous gold structures. In one experiment, cyclic voltamogram in dilute sulphuric acid has demonstrated the enhancement in surface area of a nanoporous gold electrodes (NPG) in comparison to a plain electrode. The electrode potential was scanned from negative to positive to induce the formation of an oxide layer (at approximately 1.2 Volts). The electrode potential is scanned back to the original negative potential. The reduction of the oxide formed at the electrode surface is seen as a sharp peak at approximately 0.9 Volts. A roughness factor was calculated by normalizing the area under the reduction peak against the geometric area of the electrode The enhanced surface area allows reaching very low detection limits for the detection of histamine using a co-polymer consisting of polyethylenglycol diacrylate, vinylferrocene, diamine oxidase and horseradish peroxidase. The enzymes DAO and HRP are polymerized in situ together with the electrochemical mediator vinyl ferrocene in a matrix of poly(ethylene glyclol diacrylate). While first histamine sensitivity tests conducted in a model solution showed poor performances, the lower limit of detection achievable is considerably enhanced by increasing the surface area of the sensor through nanoporous gold (NPG) layer formation.

In one example, the preparation of the NPG layer includes a plating solution including $0.1M\ Na_2S_2O_3/0.6\ M\ Ag/0.3\ M\ Au$ prepared in double distilled water fresh before each deposition round. A bare gold electrode is first electrochemically cleaned in 0.5 M sulfuric acid, rinse in water, dried and immersed in the plating solution. A potential of 0.25 Volts with respect to Ag/AgCl reference electrode is applied for 60 minutes. Silver is removed from the resulting layer by immersing the electrode in 70% nitric acid for 60 minutes.

In a further example, the preparation of the sensing layer includes a 1% vinyl ferrocene solution containing 2% AIBN and 0.5% glutaraldehyde prepared in poly(ethylene glycol diacrylate), which is sonicated to dissolve vinyl ferrocene and vortexed to ensure proper mixing. The enzyme solution is prepared by mixing 22 milligrams (mg) of diamine oxidase (DAO) and 1 mg of horseradish peroxidase (HRP) in 50 microliters (µL) of PBS to result in a 22U/milliliters (mL) DAO and 3000U/mL HRP mixture. A stir bar is added and 200 µL of the polymerization solution is added dropwise to the DAO/HRP mixture to form a uniform paste. The mixture is then constantly mixed for 2 hours at 4° C. A drop of the polymerization solution is deposited onto a 3 millimeter (mm) in a diameter gold electrode that is modified with a self-assembled monolayer of allyl mercaptan, and which is spread evenly across the electrode surface with a fluorinated glass cover slip. The electrode is exposed to UV light for 5 minutes to initiate polymerization and to entrap the enzymes in a crosslinked ferrocene-modified PEG network. The electrode is rinsed in 40% DMSO prepared in water to remove any non-polymerized monomer and loosely trapped enzyme. The electrode is finally thoroughly rinsed in water and stored in PBS at 4° C.

The fabricated sensors show very good ferrocene-enzyme communication. Histamine is measured by following the ferrocene reduction current as DAO catalyzes histamine and produces hydrogen peroxide, which is further used by HRP. However, to increase sensitivity, the sensor surface area is increased, using NPG. The fabricated electrodes are optionally further modified with the enzymes polymerization mixture. According to an alternative embodiment, the electrodes are interdigitated for enhanced transduction.

One benefit of the above described biomolecular sensor, which is directed to the detection of early signs of allergic reaction and anaphylaxis, is related to the direct wiring of histamine oxidase onto nanoporous gold electrodes. The direct wiring results in the electrodes exhibiting great sensitivity that is relevant to the measurement of histamine in whole blood. Another benefit of the sensor is that one of its applications is in the food industry for measuring product freshness of, for example, meat and fish.

According to an alternative embodiment, the biosensor is integrated with an interstitial fluid-sampling device. For example, the sampling device is in the form of an array of plain and/or hollow micro-needles that collect interstitial fluid passively. Alternatively, the array of micro-needles generate and/or collect interstitial fluids actively via an electric field, such as in iontophoresis or by heat (to degrade biological tissue and extract the fluid).

In another alternative embodiment, the biosensor is a different entity than the micro-needle array. Hollow micro-needles are used to drive interstitial fluid to the biosensor, which is located at the back of the micro-needles. The micro-needles drive the interstitial fluid either passively, by diffusion, and/or actively, via an electric field, such as in iontophoresis or by heat (to degrade biological tissue and extract the fluid).

In yet another alternative embodiment, the biosensor is a part of the micro-needle array, with each micro-needle being an individually addressable self-contained biosensor. In the preparation of an electrochemical micro-needle biosensor, each needle includes an independently addressable working macro- or micro-electrode. All micro-needles optionally share a common counter and/or a common reference electrode to perform the measurement.

In a further alternative embodiment, the biosensor is inserted under the skin with an insertion device. The insertion device is, for example, a device similar or identical to those used for insertion of glucose sensors in continuous glucose monitoring devices.

In another further alternative embodiment, the biosensor is not part of a wearable device. Instead, the biosensor is a different entity than the sampling device. Optionally, the biosensor is integrated in a portable device to enable point-of-care monitoring of the patient, for example, at home or in clinical settings.

For an exemplary sensor construction, the detection of histamine relies on the production of hydrogen peroxide by diamine oxidase in the presence of histamine, followed by subsequent oxidation of the enzyme HRP when reacting with the hydrogen peroxide produced. The redox state of HRP is measured using the mediator ferrocene. Enzymed horseradish peroxidase and diamine oxidase are copolymerized with poly(etyleneglycol) diacrylate, vinyldferrocene and photoinitiator at the electrode surface. The modified electrode is tested in the presence of the various concentration of histamine, and potential interferents, such as ascorbic acid. The sensitivity of the sensor is enhanced by increasing the surface area of the electrode, by forming a layer of nonoporous gold.

Figure 7:
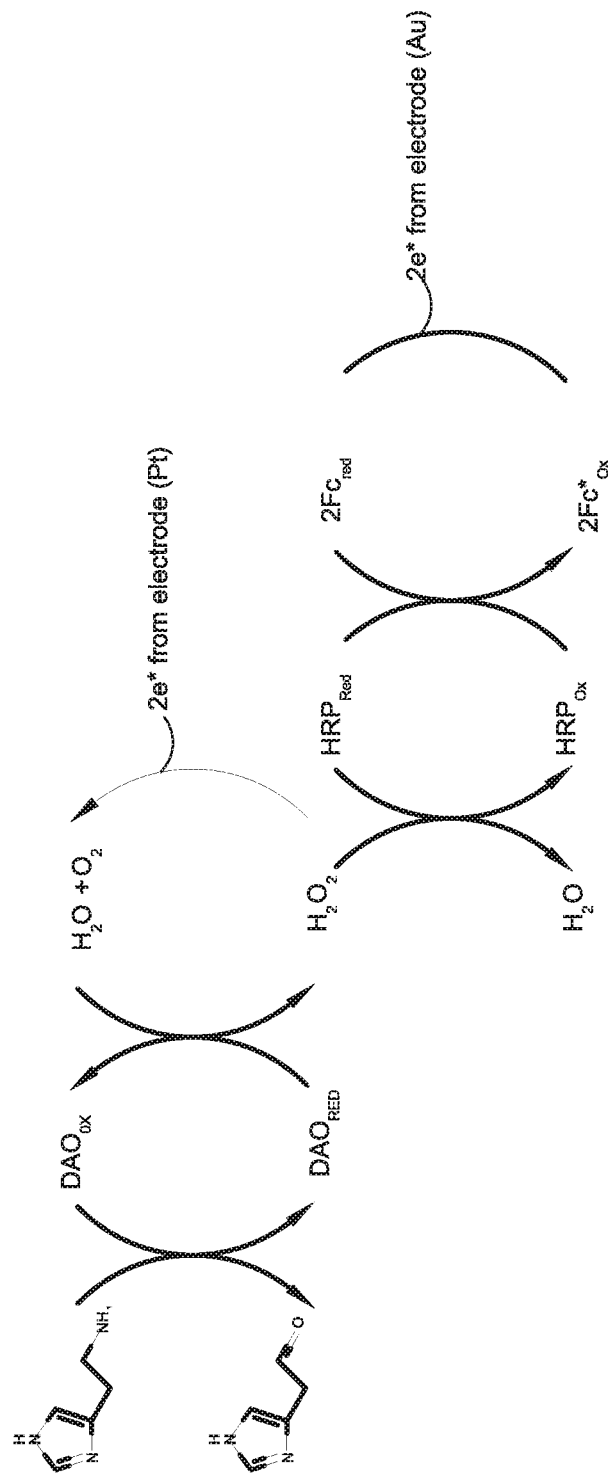
FIG. 7 is a diagram illustrating a standard DAO histamine detection mechanism with planar electrodes.

Referring to FIG. 7, a standard DAO histamine detection mechanism has planar electrodes that, by way of example, require high-detection potential for Pt electrodes which make the sensors very susceptible to interferences from other electrochemically active compounds that might be found in biological fluids. The electrodes are not limited by electrode material and optionally include a mediating layer to reduce or eliminate contribution from interfering substances. According to one example, a detection potential is at −0.36V vs. AgAgCl reference electrodes.

Figure 8:
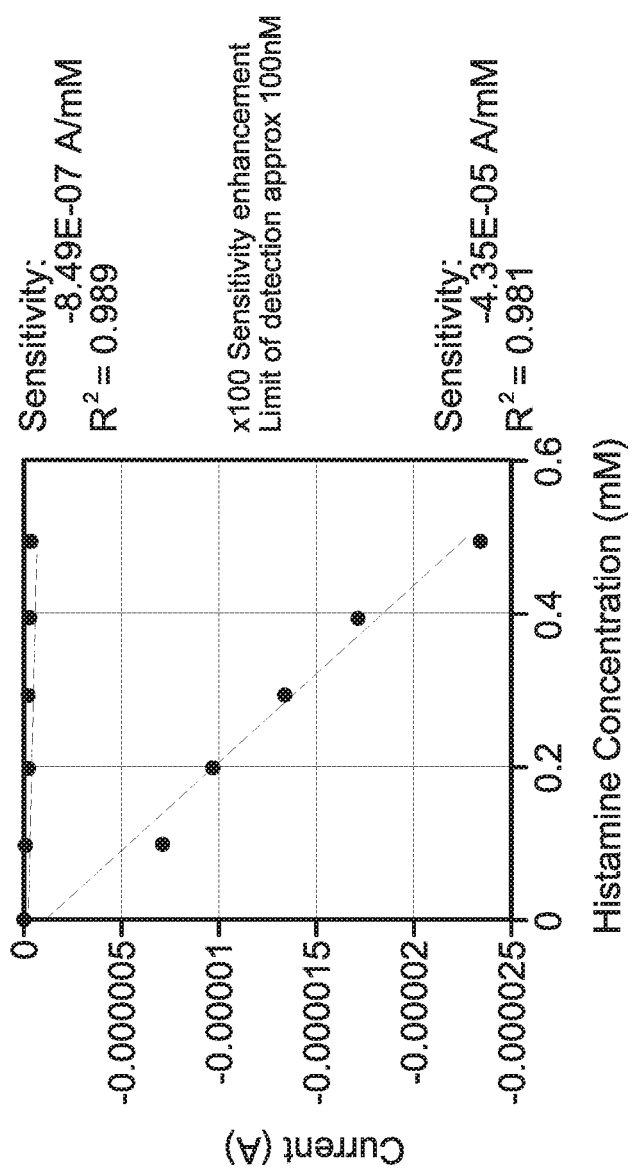
FIG. 8 is a plot showing a calibration curve of flat vs. NPG gold sensors.

Referring to FIG. 8, histamine sensitivity of NPG on planar electrodes is illustrated in a flat vs. NPG gold sensors calibration curve. For a low histamine concentration, the sensitivity is −8.49e−07 A/mM, with $R^2$=0.989. For a higher histamine concentration, the sensitivity is −4.35e−05 A/mM, with $R^2$=0.981. The curve has ×100 sensitivity enhancement and limits of detection of approximately 100 nM.

According to one exemplary embodiment, the sensor is optionally an automated breathing and bio-sensed auto-injector of epinephrine. To detect the asthma severity estimation, a two-step process includes the detection of artifacts in the recorded signals and the subsequent estimation of the HASS score is applied. The first step is the windowing of BCH, PPG, ECG, or RESP data, and the second step is the artifact detection, after which data is discarded and the HASS estimation is performed.

For processing pipelines, the detection of artifacts and the estimation of the HASS score are both implemented as machine learning pipelines. The performance is assessed by comparing the estimated HASS score to a ground truth HASS score given by a physician. Thus, initially a feature extraction is performed from the BCH, PPG, ECG, or RESP data, and, then, a feature selection is performed. From the selected features, a classification model is obtained, and a target score is compared to a ground truth score.

For artifact detection and labeling of ECG and RESP signals, features are derived to identify corrupted signals. Those features are designed to represent, by way of example, signal characteristics indicative of clipping, high-frequency noise, baseline drift, periodicity, unusual shape, and missing segments.

For artifact detection ECG, artifacts in the ECG signal are detected with high reliability. For example, prediction outcomes show an accuracy of at least about 81%, a sensitivity of at least about 72%, and a specificity of at least about 83.8%.

Figure 9A:
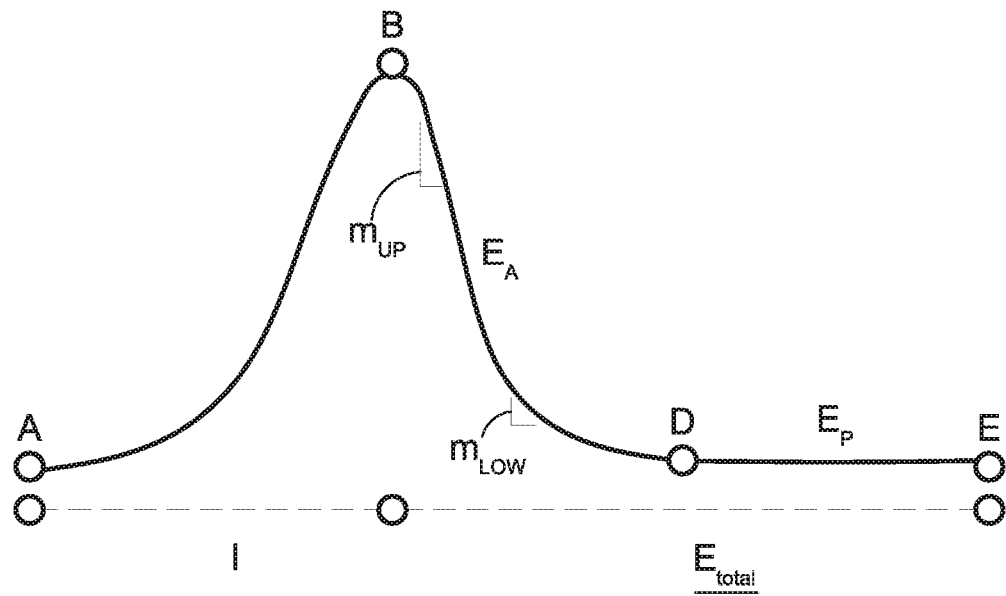
FIG. 9A is a plot showing features from normal breathing signals that are derived from Hospital Asthma Severity Scores ("HASS").
Figure 9B:
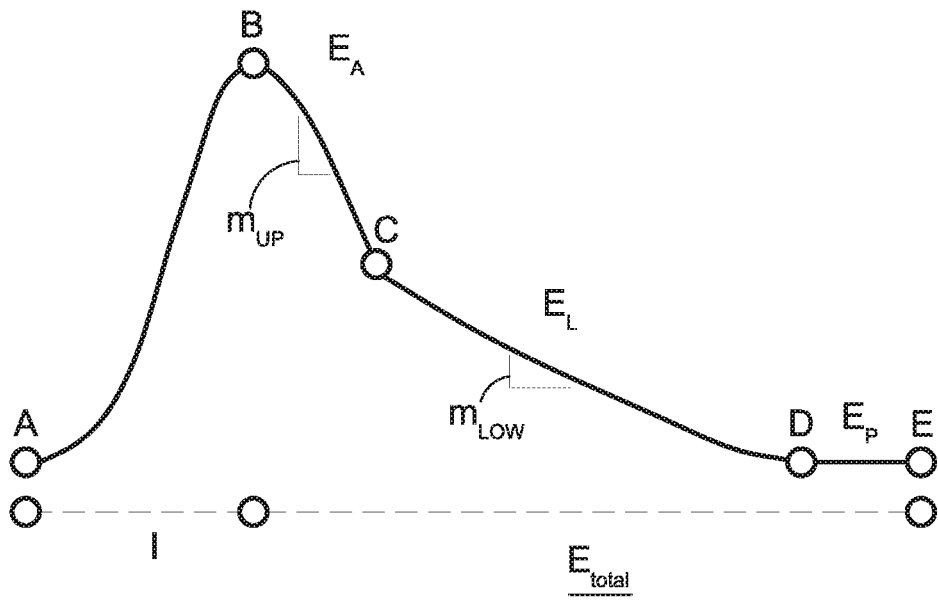
FIG. 9B is a plot showing features from obstructed breathing signals that are derived from HASS scores.

Referring to FIGS. 9A and 9B, HASS estimation is illustrated in reference to features respiration. The features from the respiration signals are derived to calculate the HASS scores, with normal breathing being illustrated in FIG. 9A and obstructed breathing being illustrated in FIG. 9B.

Figure 10A:
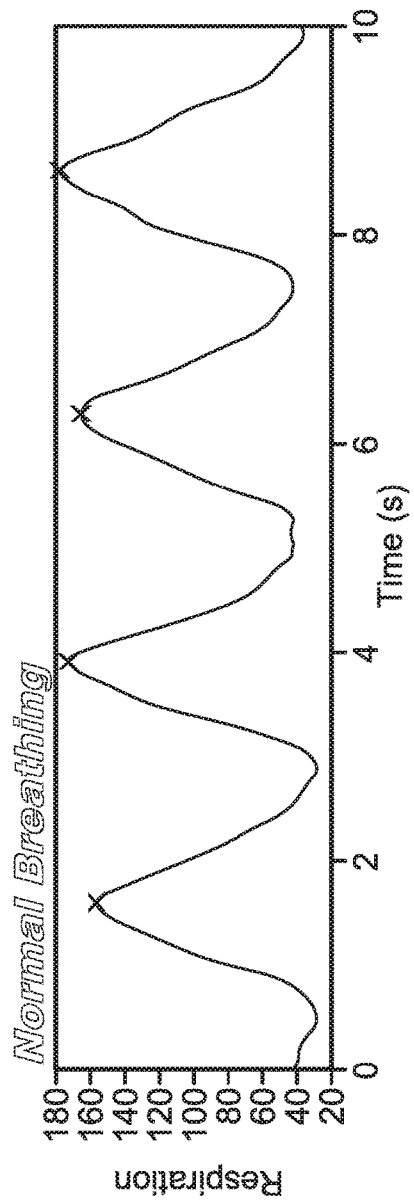
FIG. 10A is a plot showing an example of respiration signals for normal breathing.
Figure 10B:
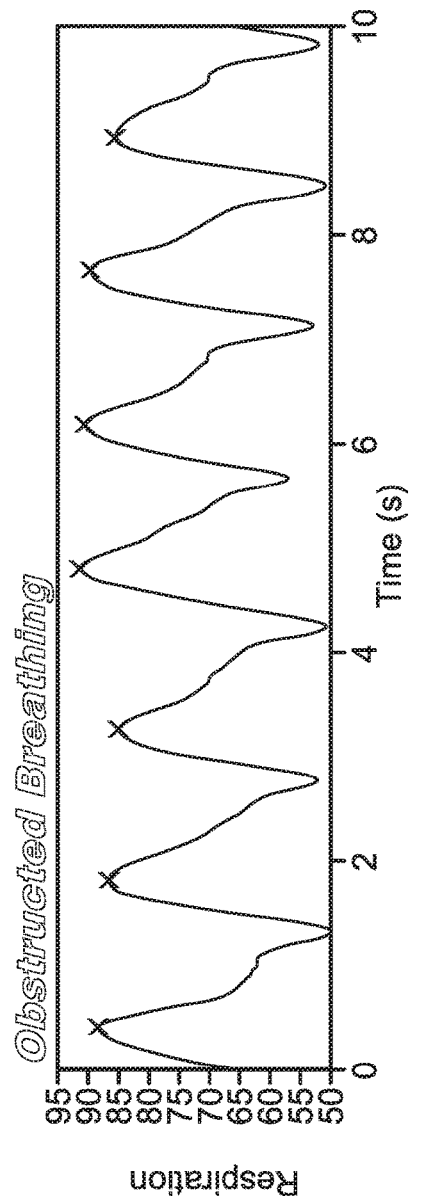
FIG. 10B is a plot showing an example of respiration signals for obstructed breathing.

Referring to FIGS. 10A and 10B, HASS estimation is illustrated in reference to respiration signals. The illustrated plots shows an example of respiration signals for normal breathing (FIG. 10A) and obstructed breathing (FIG. 10B).

Referring to FIGS. 11A and 11B, HASS estimation is illustrated in reference to features ECG. The illustrated plots shows an example of ECG signal for normal breathing (FIG. 11A) and obstructed breathing FIG. 11B).

Figure 12:
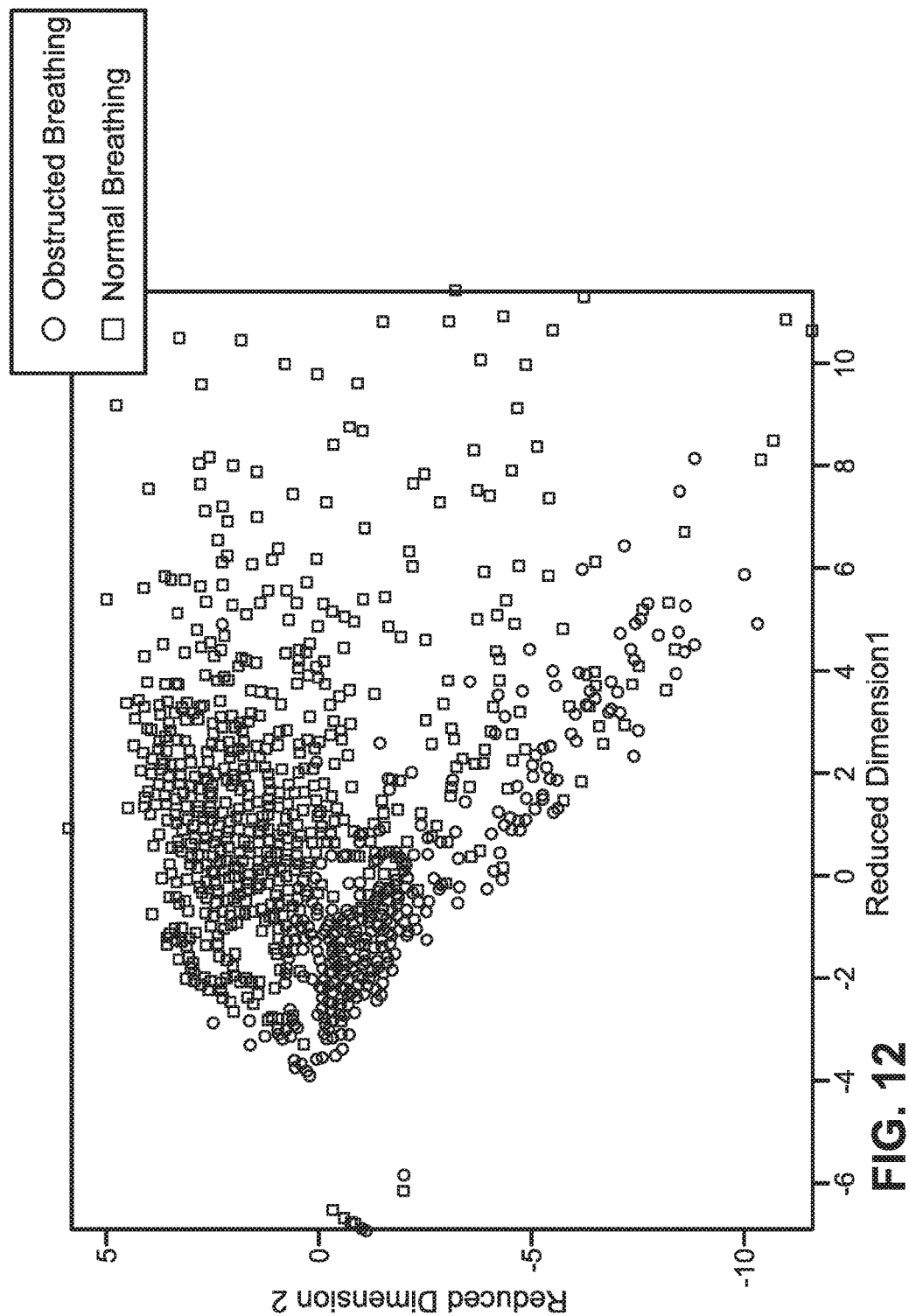
FIG. 12 is a plot showing a visual separation between normal and obstructed breathing.

Referring to FIG. 12, a plot illustrates a clear visual separation between normal and obstructed breathing. The separation is achieved by reducing multiple features derived from a respiration signal to two dimensions (e.g., Reduced Dimension 1 and Reduced Dimension 2).

Figure 13:
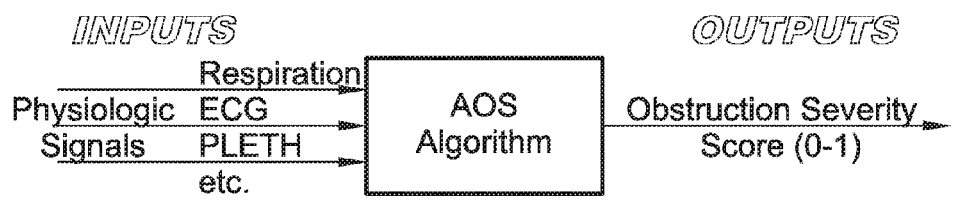
FIG. 13 is a diagram showing an airway obstruction severity ("AOS") algorithm.

Referring to FIG. 13, an AOS algorithm uses various physiologic signals as input to calculate the severity of airway obstruction in a person wearing the medical device described above. The AOS algorithm outputs an obstruction severity score on a scale of 0 to 1, where 0=healthy and 1=extremely obstructed. The AOS algorithm is embedded onto the medical device. Because airway obstruction is a major symptom of anaphylaxis, the AOS algorithm is also a key module in the anaphylaxis detection device. Additionally, airway obstruction is a symptom of asthma and is optionally used in an asthma monitoring device.

Figure 14:
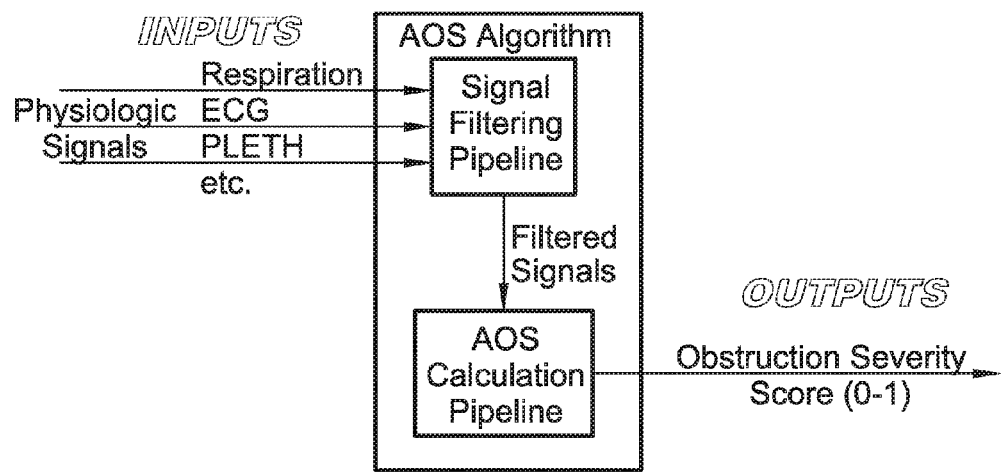
FIG. 14 is a diagram showing the AOS algorithm of FIG. 13 containing two machine learning pipelines.

Referring to FIG. 14, the physiologic input signals to the AOS algorithm include (but are not limited to) the following: electrocardiogram (ECG), respiration (chest wall movement), and pulse plethysmograph (PLETH) waveforms. The AOS algorithm contains two classical machine learning pipelines operating in series, as illustrated in FIG. 14.

Referring to FIG. 15, the first pipeline is used to filter outliers and noise from the incoming physiologic signals, and the second pipeline is used to calculate the AOS score. Each pipeline uses a classical machine learning technique.

After filtering the signal, the first step in an AOS Calculation Pipeline is to extract features that can be expressed numerically and that correlate with obstructed breathing. The features are calculated on a segment of the physiologic input signals and plugged into a feature selection model. The goal of the feature selection model is to optimize the performance of the AOS algorithm to effectively predict the severity of airway obstruction. This is achieved by selecting a subset of features that are sufficient to accurately describe the intrinsic behavior of the observed breathing patterns. A supervised learning approach using the reduced feature set in conjunction with ground truth information about the presence and severity of obstructed breathing (e.g., derived from a clinical expert) allows the AOS algorithm to generate a predictive model which can be applied for the autonomous and objective evaluation of breathing obstruction severity.

Referring to FIG. 16, exemplary physiologic features are used in the AOS algorithm. The features include inspiratory to expiratory time ratio (I:E), the inspiratory and expiratory times referring to the periods during which a patient inhales (I) and exhales ($E_{total}$).

Another way of characterizing the structural changes of the respiratory waveforms associated with obstructed breathing is established by calculating statistical features like the mean, standard deviation, range, skewness, kurtosis and the entropy of each breath. These additional statistical features are not included in the table of FIG. 16, but are used in the machine learning framework.

Through statistical analyses of the features seen in the table of FIG. 16, several features are identified, such as the upper respiratory slope that shows statistically significant differences (p-value<0.05) between normal and obstructed breathing. Additionally, referring to FIG. 12, the information content of multiple features derived from the respiration signal is reduced into two dimensions, which shows a clear separation between normal and obstructed breathing. Furthermore, a machine learning classification model is applied that enables the autonomous discrimination between respiration signals having normal and obstructed breathing with high reliability (accuracy, sensitivity, and specificity above 82%). These results indicate that the features extracted from the respiration waveform are able to represent physiologic changes associated with airway obstructions. This demonstrates that the AOS algorithm reliably detects obstructed breathing, and is a relevant part of the anaphylaxis detection and treatment device.

Referring to FIG. 17, the ECG and PLETH waveforms change during periods with obstructed breathing due to the associated stress on the body. Therefore, a variety of physiologic characteristics, such as those displayed in the table of FIG. 17, are derived from the ECG and the PLETH waveforms. Similar statistical characteristics (mean, standard deviation, etc.) used for the respiratory waveforms are also calculated to characterize the structural changes in the ECG and PLETH waveforms. These characteristics are optionally used as input for a machine learning model to automatically classify the severity of airway obstruction.

Additional features from the respiration, ECG, and PLETH waveforms are calculated using a point-process method, which is a stochastic process that continuously characterizes the intrinsic probabilistic structure of discrete events and that has been successfully applied to study a wide range of phenomena, analyzing data such as earthquake occurrences, traffic modeling, and neural spiking activity. More recently, the utility of point process theory has been validated as a powerful tool to estimate heart beat and respiratory dynamics—including instantaneous measures of variability and stability—even in short recordings under nonstationary conditions.

In contrast, the commonly used standard methods are primarily applicable for stationary data or provide only approximate estimates of the dynamic signatures that are not corroborated by goodness-of-fit methods. Few methods are available for time-frequency analysis of nonstationary data (e.g., Hilbert-Huang and Wavelet transforms). However, these methods need to be applied to short batches of data, making them less suitable for tracking dynamics in real time. Finally, the point process framework allows for inclusion of any covariate at any sampling rate, and we will take advantage of this property to generate instantaneous indices as well as power spectrum indices.

Figure 18:
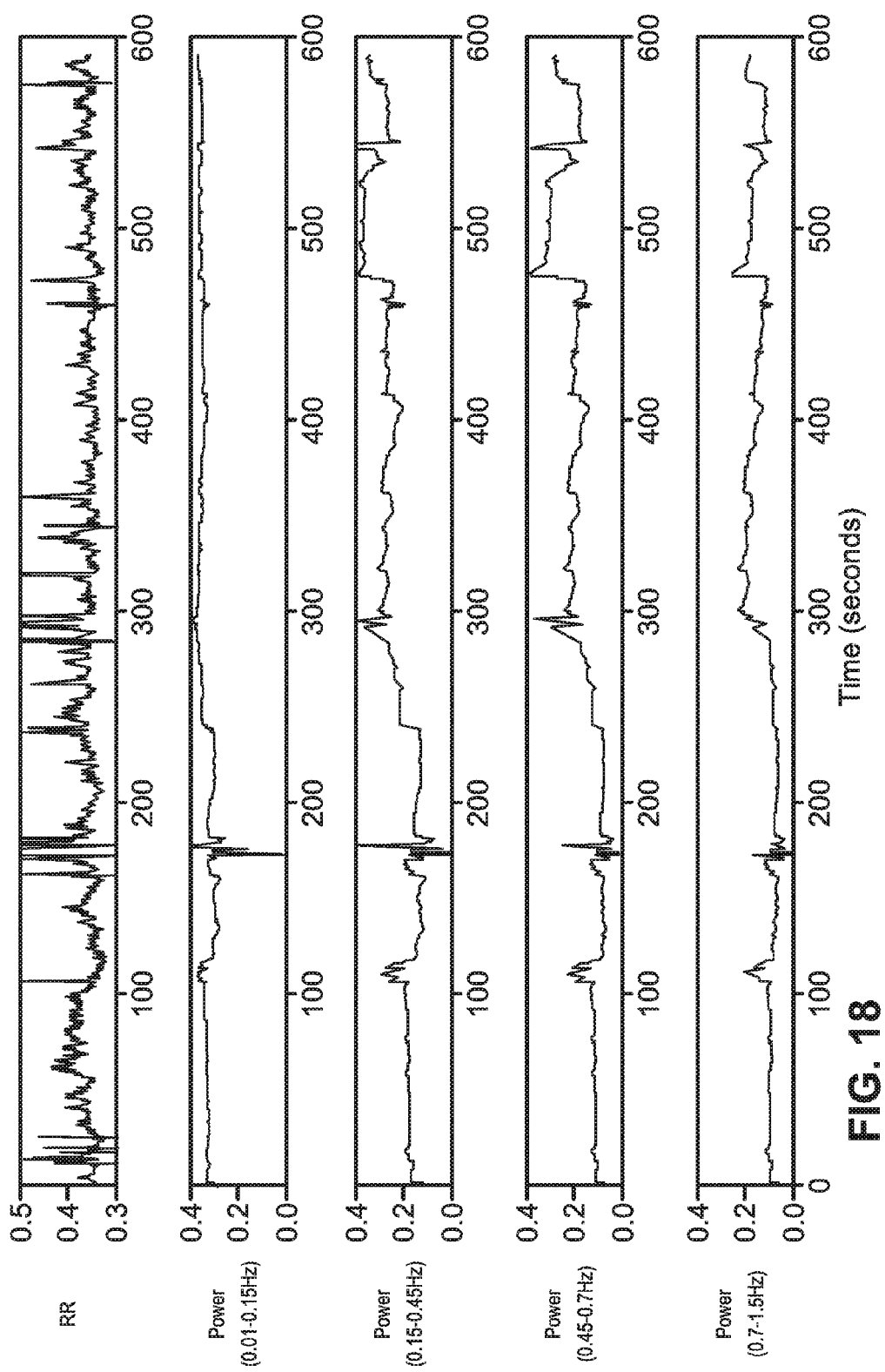
FIG. 18 is a plot showing a 4 RR interval along with power calculated at four different frequency ranges.

To effectively characterize the variability in ECG R wave peak intervals (RR interval), the power spectrum is calculated at different frequency ranges. FIG. 18 represents the estimation of instantaneous power at different frequency ranges along with the RR interval.

Figure 19:
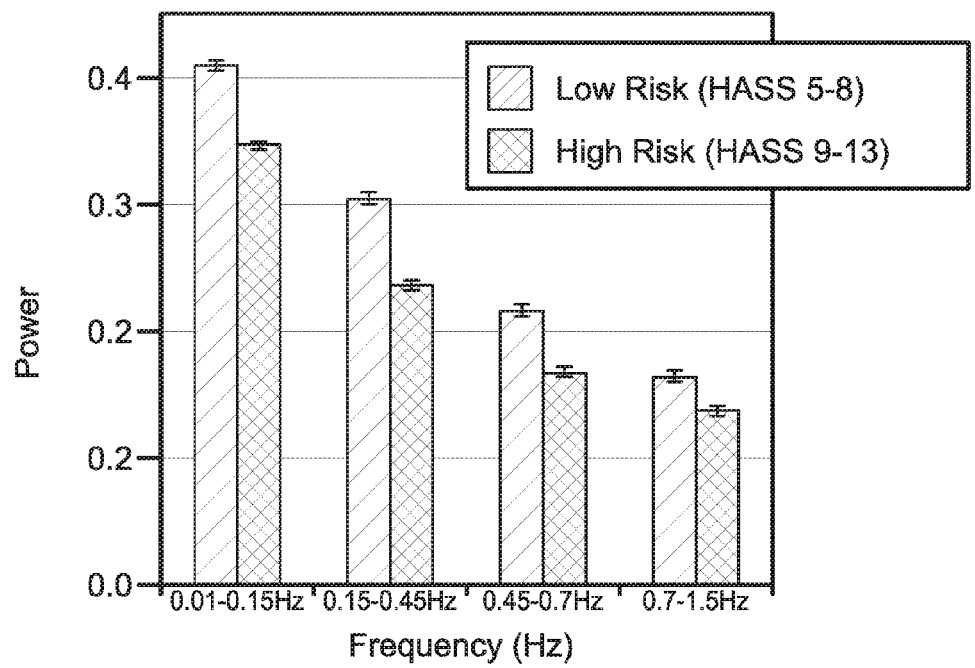
FIG. 19 is a chart showing an average power estimated using a point process model at four different frequency ranges.

Referring to FIG. 19, the average power spectrum is calculated in each of the frequency ranges, with the results showing that the power spectrums vary significantly different between "Low Risk" and "High Risk" groups. Thus, power spectrum at different frequency ranges is a relevant feature in the machine learning framework.

To obtain additional relevant features from the PLETH signal, a wavelet transform technique is further applied. The wavelet transform technique is a powerful tool for extracting amplitude or power instantaneously at multiple time scales from a nonstationary data. The power is estimated at multiple time scales based on a wavelet transform with the Morlet function as the mother wavelet. Using translational and scaling of the mother wavelet, the power is estimated at multiple time scales with a dyadic representation of scales.

Figure 20A:
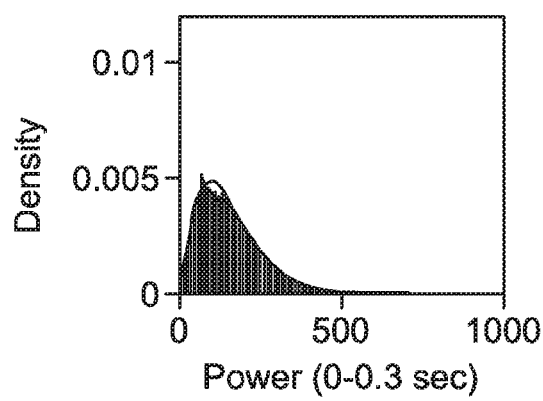
FIG. 20A is a plot showing the distribution of power at a first time scale, which follows a skewed distribution that is characterized by a Gamma function (solid line).
Figure 20B:
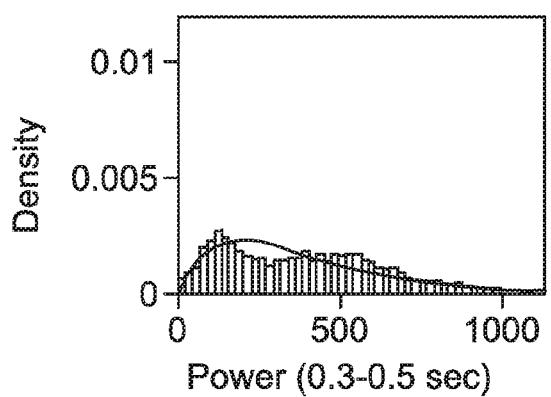
FIG. 20B is a plot showing the distribution of power of FIG. 20A at a second time scale.
Figure 20C:
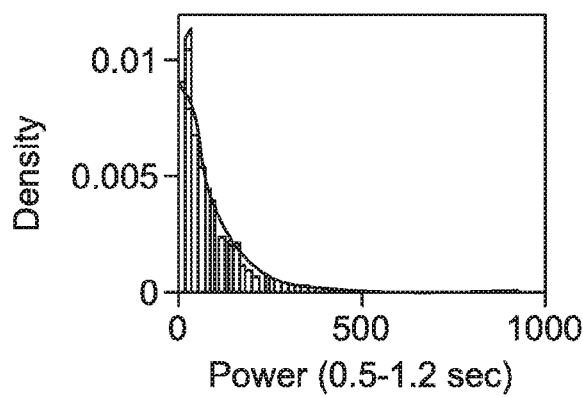
FIG. 20C is a plot showing the distribution of power of FIG. 20A at a third time scale.

Referring to FIGS. 20A-20C, it is determined that the shape parameters of the distribution at two of the time scales of the PLETH signal are significantly different between "Low Risk" vs "High Risk" group. Specifically, the distribution of power at different time scales follows a skewed distribution that is characterized by a Gamma function. Thus, the distribution of power is a relevant feature in the machine learning framework.

Figure 21:
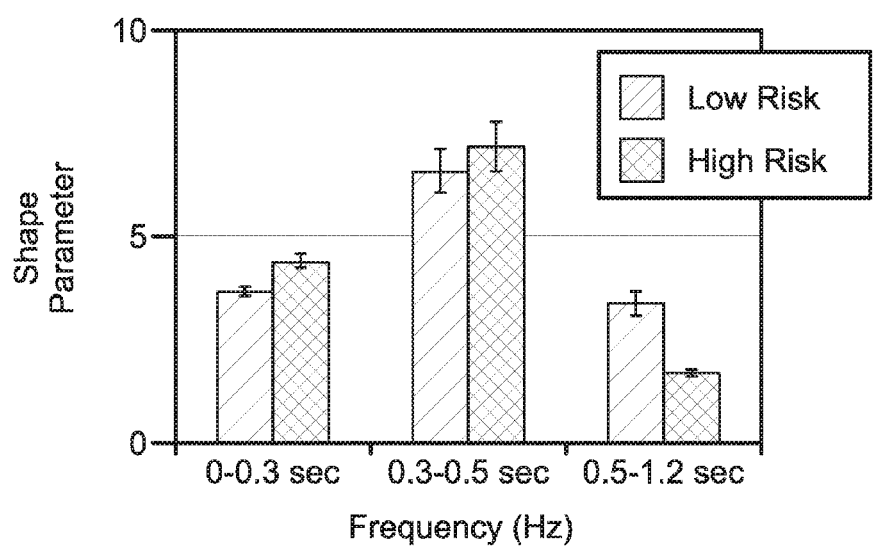
FIG. 21 is a chart showing the shape of the distribution estimated using a Gamma function of power at different time scales.

Referring to FIG. 21, the shape of the distribution of the PLETH signal estimated using the Gamma function of power at different time scales shows the significant difference between the "Low Risk" and the "High Risk" groups. Specifically, the distribution is shown in the 0-0.3 seconds range as well as the 0.5-1.2 seconds range.

Thus, a benefit of the AOS algorithm include calculating breathing obstruction severity in real-time using a combination of many breath-to-breath and heartbeat-to-heartbeat features that are averaged over time. Other benefits of the AOS algorithm include the abilities to continuously and immediately generate a breathing obstruction severity score (e.g., no calibration or "learning time" necessary). Yet other benefits of the AOS algorithm include providing a breathing obstruction severity score without a human (e.g., a clinician) and to calculate the I:E ratio, in contrast to flawed current methods. Another benefit of the AOS algorithm is the measurement of obstructed breathing, which is a symptom of many conditions, including asthma and anaphylaxis, as well as other ailments.

Referring to FIGS. 22A-22F, the sensor module includes a Smart Auto-injector device 100 with an external housing 101 that includes a motor 102, a latch/locking mechanism 104, a drive spring 106, a nitinol needle 108, a reservoir and actuator for medication delivery 110, and an adhesive patch 112. The device 100 receives a signal from a sensing module, in response to which the motor 102 unlatches the spring 106. Alternatively, instead of the motor 102, the spring 106 is unlatched in response to a manual action provided by a user.

Figure 22C:
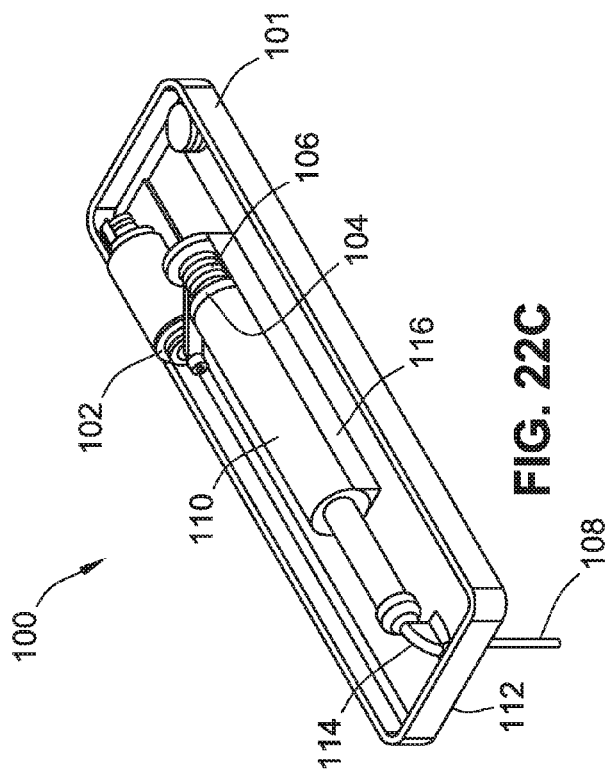
FIG. 22C is a perspective view of the smart auto-injector of FIG. 22A in a mid-operation position.
Figure 22D:
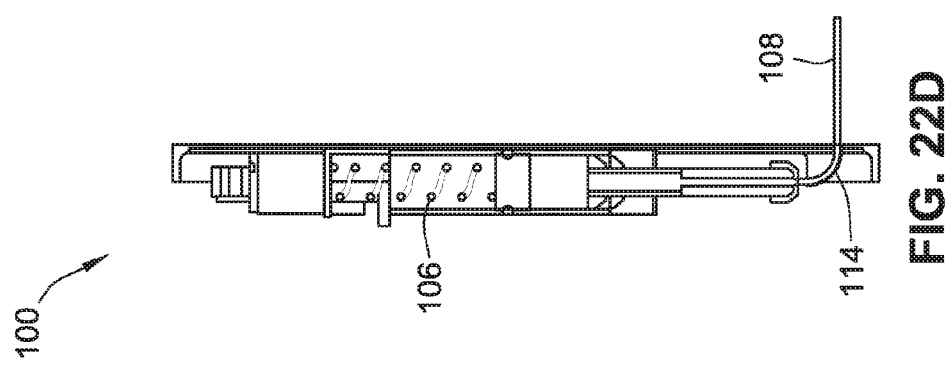
FIG. 22D is a side view of the smart auto-injector of FIG. 22C in the mid-operation position.
Figure 22E:
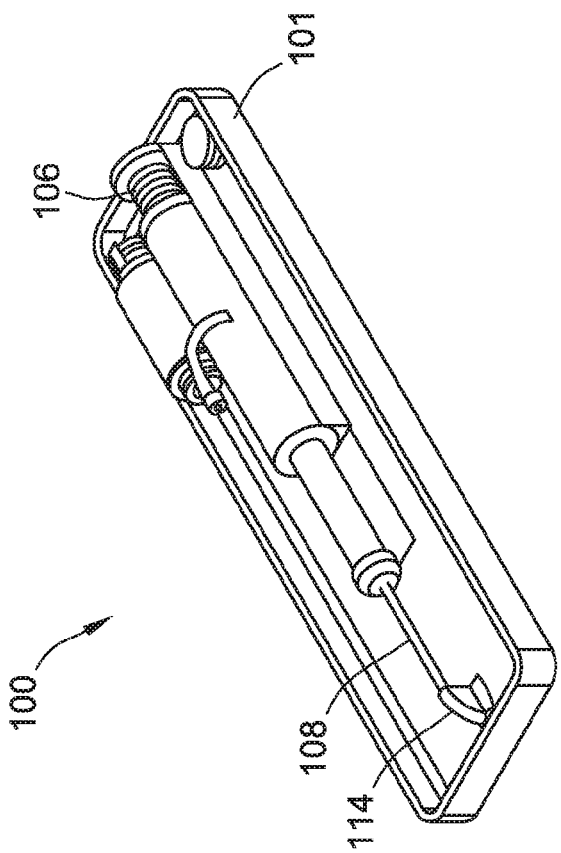
FIG. 22E is a perspective view of the smart auto-injector of FIG. 22A in a post-operation position.
Figure 22F:
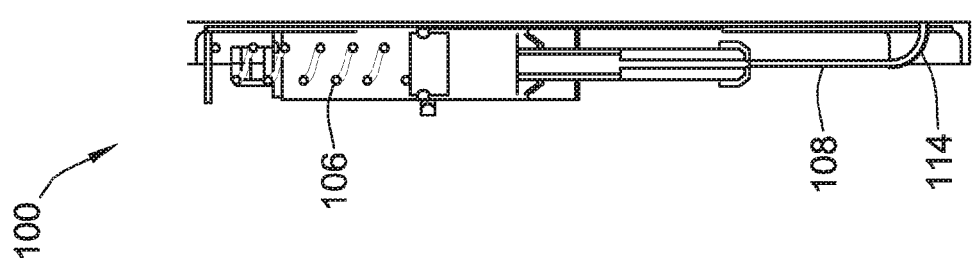
FIG. 22F is a side view of the smart auto-injector of FIG. 22A in the post-operation position.
Figure 23A:
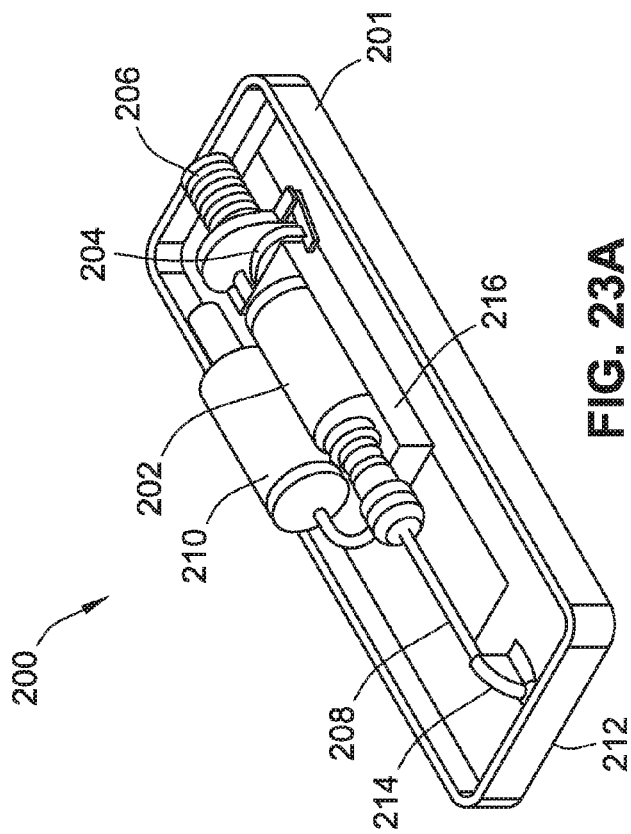
FIG. 23A is a perspective view of a smart auto-injector in a pre-operation position, according to another embodiment.
Figure 23B:
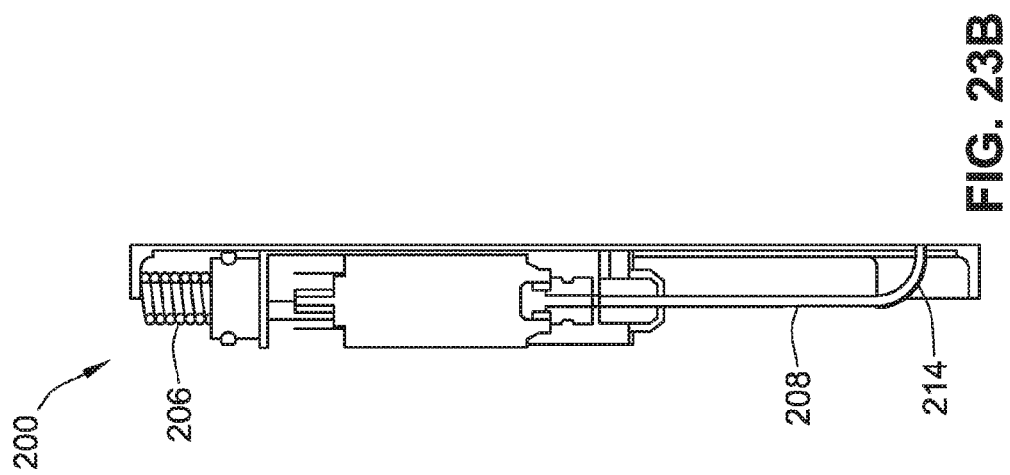
FIG. 23B is a side view of the smart auto-injector of FIG. 23A.

As specifically illustrated in FIGS. 22C and 22D, the spring 106 drives the needle 108 through a pre-shaped curve 114 for intramuscular ("IM") injection. The pre-shaped curve 114, which according to some examples is in the shape of an anvil or a channel, reshapes and drives the needle 108 for the IM injection to an IM injection depth. A relief valve (e.g., a fluid outlet) opens up due to built-up pressure or mechanical trigger. The spring 106 injects a predetermined dosage (e.g., 0.15 mg, 0.3 mg, or 0.5 mg) and the device 100 remains still for a predetermined time (e.g., 5 sec., 10 sec. or 15 sec.). A user removes the device away from the body, or the motor 102 retracts a mobile housing 116 containing the needle 108 by pulling it backwards, retracting the needle 108 into the device 100 (as illustrated in FIGS. 22E and 22F).

Some benefits of the device 100 include that it is fully wearable on the body, is discreetly hidden under clothing, has an adjustable size for different body shapes, and is suitable for multiple sites on the body. Optionally, the device 100 is configured to include hypoallergenic materials and is applicable for IM and/or subcutaneous injections. Optionally, yet, the device 100 is compatible with a smartphone for notifying emergency services, family members, and/or friends when the device 100 has made an injection.

Other benefits of the device 100 include having the needle 108 being driven through the pre-shaped curve 114 for being reshaped for IM or subcutaneous insertion at different angles. Another benefit of the needle 108 includes the super-elasticity and, potentially, the additional shape memory properties of the nitinol material for IM injections. Because one objective of this design is to minimize the height of the injector, using a super-elastic nitinol needle enables the use of a straight needle that bends 90 degrees to enter the body as it is advanced through the pre-shaped curve 114. Further, this design minimizes the height required of the injector 101, making it more likely to be worn under clothes. Optionally, the needle 108 is configured to provide a dual functionality as the needle and the medication reservoir. Additionally, the needle 108 is designed in a way that it drives itself for insertion and is retracted by an electromechanical or mechanical actuator.

According to further benefits of the device 100, a dual actuation feature is achieved by fully automating the needle insertion, the medication delivery, and the needle retraction. Additionally, the dual actuation is optionally triggered manually for the needle insertion and the medication delivery, and/or double-manually triggered for the needle insertion and medication delivery. Furthermore, the device 100 is beneficial for using hydrostatic forces for reshaping the needle through the pre-shaped curve 114 with different angles for the IM insertion.

Referring to FIGS. 23A-23G, the sensor module includes a Smart Auto-injector device 200, in accordance with an alternative embodiment, with an external housing 201 that includes a motor 202, a latch/locking mechanism 204, a drive spring 206, a nitinol needle 208, a reservoir and actuator for medication delivery 210, an adhesive patch 212, and a mobile housing 216. The device 200 receives a signal from a sensing module, in response to which the motor 202 unlatches the spring 206. Alternatively, instead of the motor 202, the spring 206 is unlatched in response to a manual action provided by a user.

As specifically illustrated in FIGS. 23C and 23D, the spring 206 drives the mobile housing 216, which contains the motor 202 and the needle 208, driving the needle 208 through a pre-shaped curve 214 for IM injection. The pre-shaped curve 214, which according to some examples is in the shape of an anvil or a channel, reshapes and drives the needle 208 for the IM injection to an IM injection depth.

As specifically illustrated in FIGS. 23E-23G, a motor shaft rotates and reels-in a cable 220 that is coupled to the passive actuator 210 for medication delivery. The cable 220 moves the passive actuator 210 downwards, injecting a predetermined dosage (e.g., 0.15 mg, 0.3 mg, or 0.5 mg) and the device 200 remains still for a predetermined time (e.g., 5 sec., 10 sec. or 15 sec.). The motor 202 retracts the needle 208 into the device 200.

Figure 24:
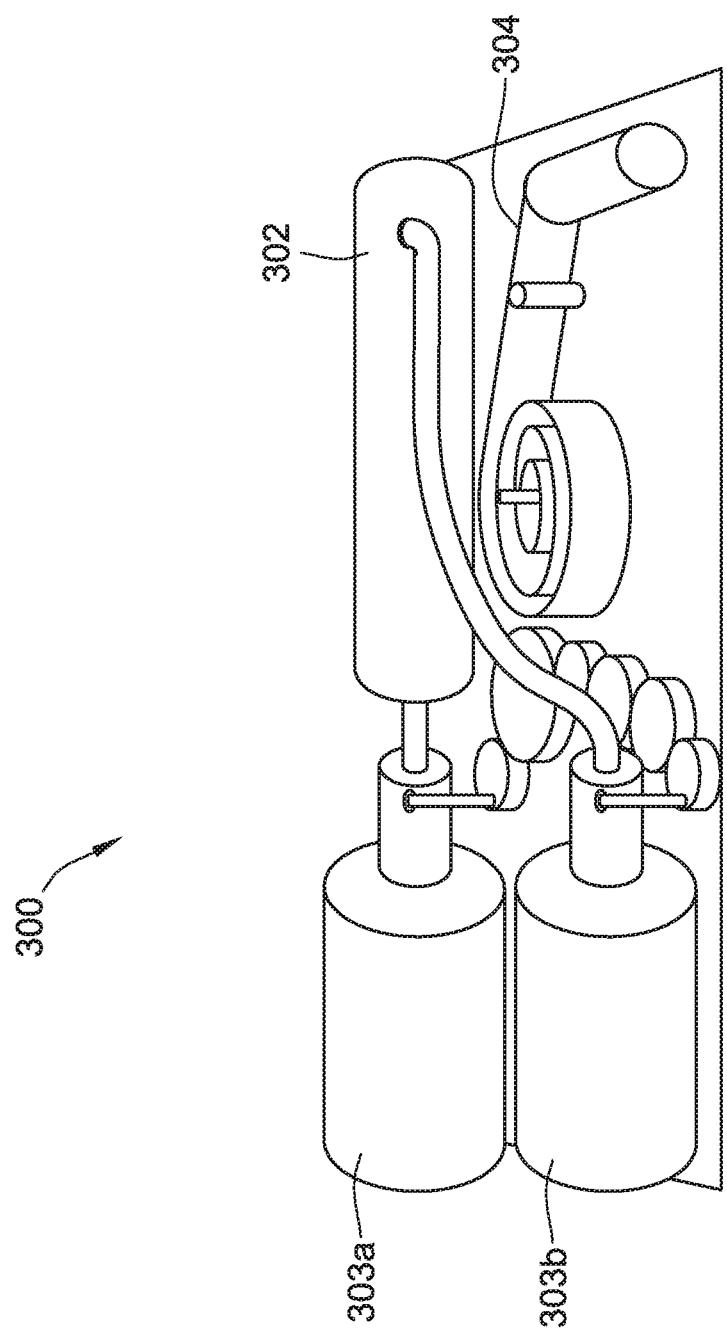
FIG. 24 is a perspective illustration of a CO2 cartridge-based actuator for a smart auto-injector, according to an alternative embodiment.

Referring to FIG. 24, the sensor module includes an alternative Smart Auto-injector device in the form of a $CO_2$ cartridge-based actuator 300 that includes a housing 302 enclosing mechanisms for a needle driver, a medication reservoir, and a medication delivery. The housing 302 is coupled to a first $CO_2$ cartridge 303a and a second $CO_2$ cartridge 303b. The actuator 300 further includes a lock/latch mechanism 304, which is operated manually or via a motor.

In operation, the actuator 300 receives a signal from a sensing module and the motorized or manual action unlatches a spring mechanism as previously described above in reference to the Smart Auto-injector devices 100, 200. The spring mechanism, motor, or other electromechanical actuator engages the first $CO_2$ cartridge 303a, which releases pressurized $CO_2$ gas to actuate the internal mechanism and drive a nitinol needle through a pre-shaped curve (as described above). The pre-shaped curve reshapes and helps drive the needle for IM injection (as described above), and the $CO_2$ cartridge 303a actuates the internal mechanism to deliver the predetermined dosage (e.g., 0.15 mg, 0.3 mg, or 0.5 mg) of medication when the needle insertion is completed. The second $CO_2$ cartridge 303b is, then, engaged, to reverse the internal mechanism and retract the needle back into the device immediately after the medication delivery ends. A benefit of the $CO_2$ cartridges 303a, 303b is that they act as actuators for driving one or more of the medication insertion, the needle insertion, and the needle retraction.

Figure 25A:
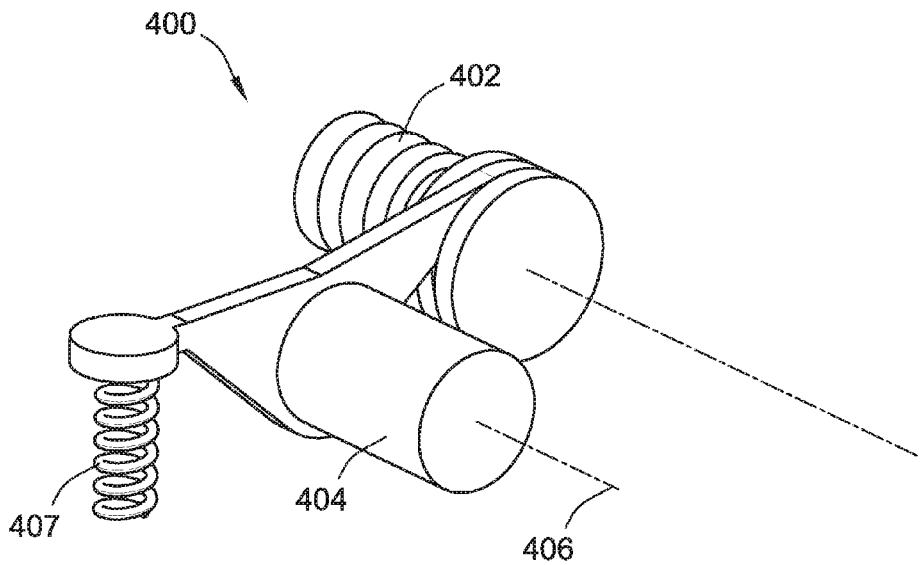
FIG. 25A is a perspective illustration of a lock/latch mechanism for a smart auto-injector, according to another alternative embodiment.
Figure 25B:
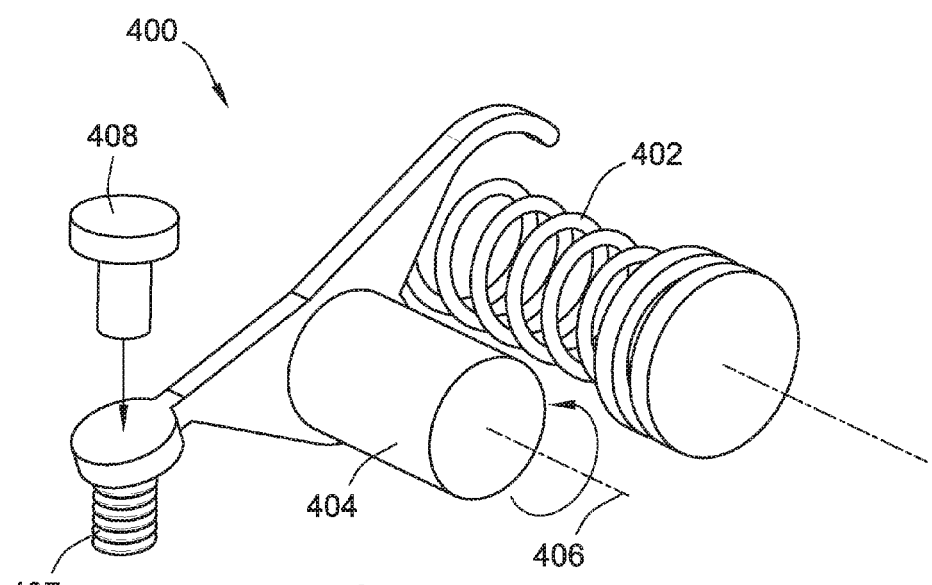
FIG. 25B shows the lock-latch mechanism of FIG. 25A after applying a push force.

Referring to FIGS. 25A and 25B, the sensor module includes another alternative Smart Auto-injector device that has a lock/latch mechanism 400 with a driver spring 402, a motor 404 mounted along a pivot axis 406, and a lock spring 407. The lock/latch mechanism 400 allows the device (as described above) to be triggered by the motor 404 in a fully automatic manner. Optionally, as a safety measure, the device is also triggered manually by using a multiple-layered safety switch 408.

Referring to FIG. 26, the sensor module includes an alternative Smart Auto-injector device that has a rack and pinion mechanism 500 with a motor 502, a reservoir 504, a spring for medication delivery 506, and a needle 508. The motor 502 drives the rack and pinion mechanism 500 to drive the needle 508 through a pre-shaped curve for reshaping the needle 508 for IM injection. At the end of the needle insertion motion, the spring 506 is released and the predetermined dosage of medication is delivered. The device remains still for a predetermined time period and, then, the motor 502 retracts the needle 508 back into the device from the human body.

Figure 27:
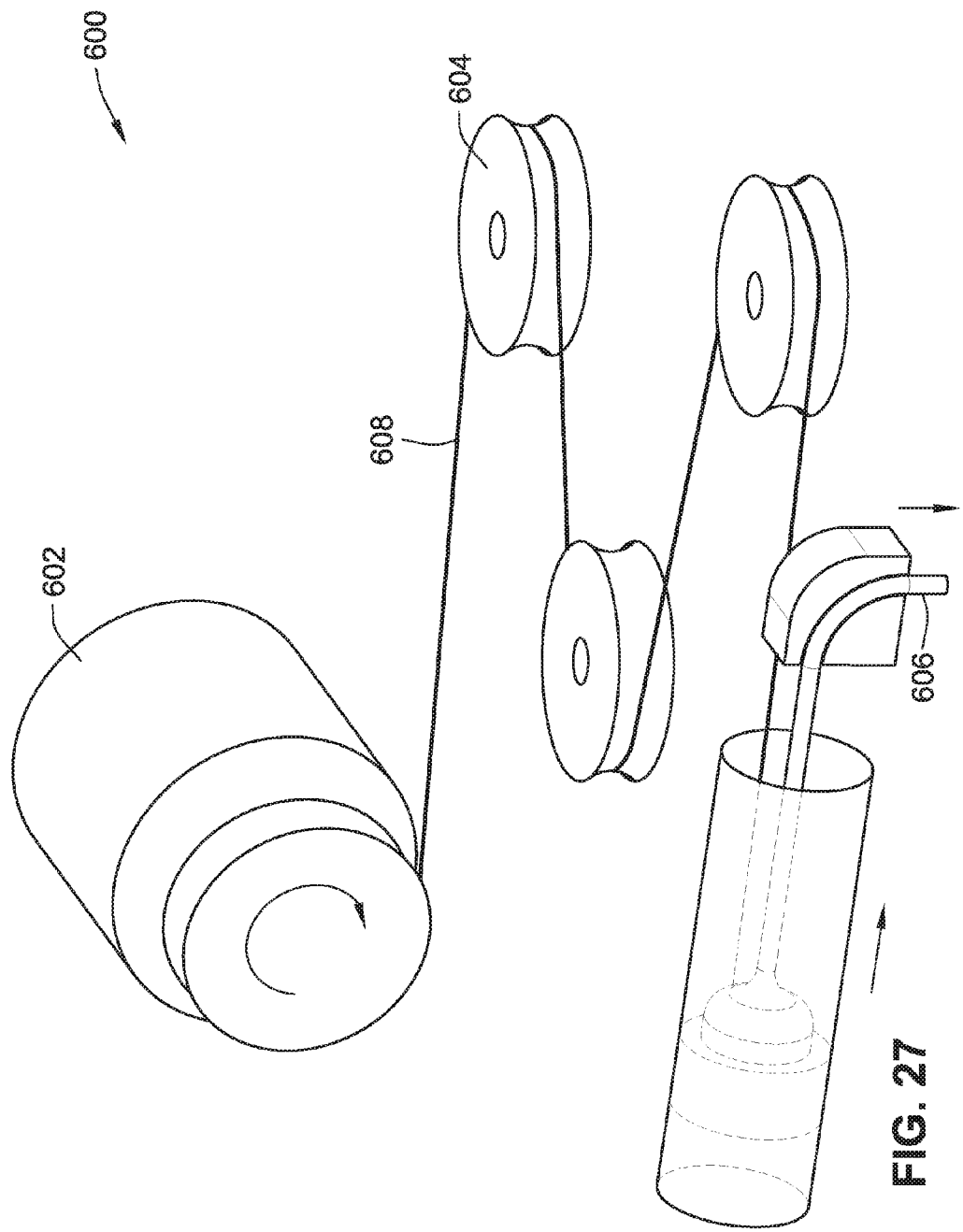
FIG. 27 is a perspective illustration of a pulley mechanism for a smart auto-injector, according to another alternative embodiment.

Referring to FIG. 27, the sensor module includes another alternative Smart Auto-injector device that has a pulley mechanism 600 with a motor 602, a plurality of pulleys 604, and a needle 606. The motor 602 drives one or more cables 608 to drive the needle 606 through a pre-shaped curve for reshaping the needle 606 for IM injection. At the end of the needle insertion motion, a spring for medication delivery is released and a predetermined dosage of medication is delivered. The device remains still for a predetermined time period and, then, the motor 602 triggers a mechanism to retract the needle 606 back into the device from the human body.

Referring to FIG. 28, the sensor module includes another alternative Smart Auto-injector device that has a worm-gear mechanism 700 with a motor 702, a worm gear 704, a linkage 706, a driving mechanism 708 (including a reservoir and medication delivery), and a mechanical stop 710. The motor 702 drives the worm-gear mechanism 700 to drive a needle through a pre-shaped curve for reshaping the needle for IM injection. Then, the driving mechanism 708 hit the mechanical stop 710 and a predetermined dosage of medication starts to be delivered. The device remains still for a predetermined time period, and, then, the motor 702 retracts the needle back into the device from the human body.

Figure 29A:
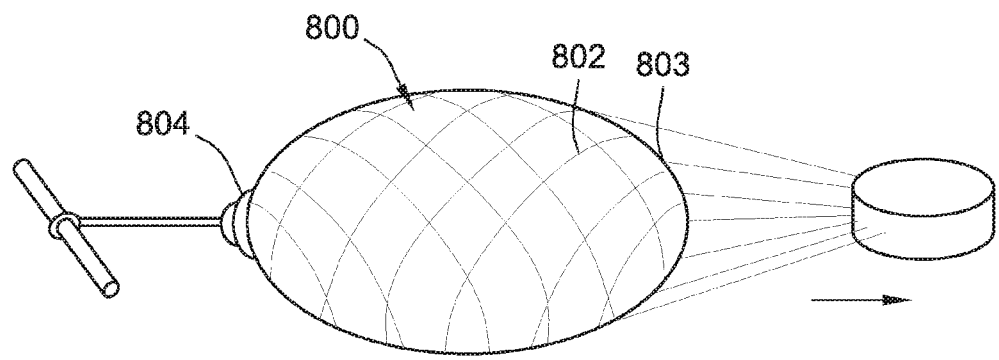
FIG. 29A is a perspective illustration of a squeezable pouch for a smart auto-injector, according to another alternative embodiment.
Figure 29B:
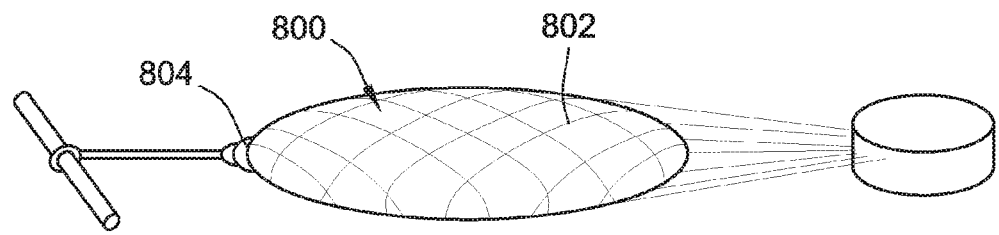
FIG. 29B shows the squeezable pouch of FIG. 29A in a squeezed position.

Referring to FIGS. 29A and 29B, the sensor module includes another alternative Smart Auto-injector device that has a collapsible pouch 800 as a reservoir. The pouch 800 is wrapped with a wire mesh 802 that is made of nitinol or stainless steel. The pouch 800 is fixed at a position in a reservoir housing and the wire is attached to a mechanical or electromechanical actuator. When the actuator starts working for delivering the medication, the array of wires is pulled to squeeze the pouch 800. The pressure inside the pouch 800 is increased, and based on the increased pressure, a fluid outlet 804 opens to deliver the medication into the body through a nitinol needle. The pouch 800 further includes a fluid inlet 803 for refilling. Alternatively, the pouch 800 lacks the wire mesh 802, but includes other physical features for applying pressure to the pouch 800 to collapse and open the fluid outlet 804.

Figure 30:
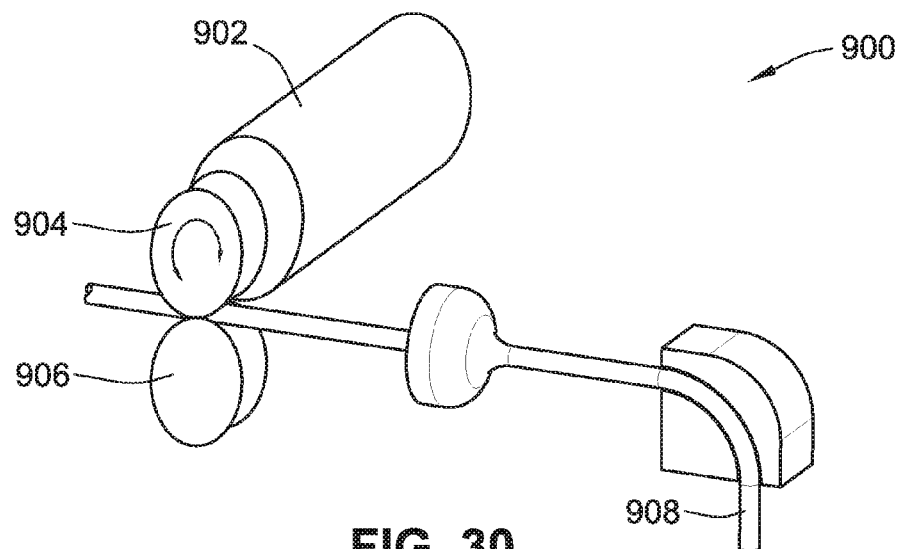
FIG. 30 is a perspective illustration of a friction drive for a smart auto-injector, according to another alternative embodiment.

Referring to FIG. 30, the sensor module includes another alternative Smart Auto-injector device that has a friction drive 900 with a motor 902, a friction wheel 904, a guide wheel 906, and a needle 908. The motor 902 drives the friction wheel 904 that is coupled by surface friction to the needle 908. The rotation of the friction wheel 904, thus, drives the needle 908 through a pre-shaped curve for reshaping the needle 908 for IM injection. The needle 908 is guided at the motor level by the guide wheel 906, which is freely rotating. At the end of the needle insertion motion, the predetermined dosage of medication is delivered through electromechanical or mechanical means. The device remains still for a predetermined time period, and, then, the motor 902 drives the friction wheel 904 in an opposite direction to retract the needle 908 back into the device.

Consistent with the above disclosure, benefits of the described devices include retracting a needle with electromechanical components (e.g., motors, solenoids, piezoelectric actuators, linear motors, etc.) or with mechanical actuators (e.g., springs, pistons, jets, $CO_2$ cartridges, etc.). By way of example, electromechanical drives include cables pulled by a motor that drives the needle for insertion and retraction through a pulley system that provides a lower profile and a mechanical advantage, as illustrated in FIG. 27. In another example, an electromechanical drive includes a needle driven by a two-way motor for the insertion, medication delivery, and retracted, as illustrated in FIGS. 23A-23G. In yet another example, an electromechanical drive includes a direct drive with a rack-and-pinion and a mechanical actuator-driven medication injection, as illustrated in FIG. 26. In yet another example, an electromechanical drive includes a direct drive with a friction and a mechanical actuator-driven medication injection, as illustrated in FIG. 30. In yet another example, an electromechanical drive includes a direct drive with a worm gear to drive the needle for insertion and retraction, and a mechanical actuator-driven medication injection, as illustrated in FIG. 28.

A further benefit of the described devices includes having an adjustable dosage for medication delivery (e.g., 0.15 mg, 0.30 mg, 0.5 mg), which is adjustable manually or via software. Yet another benefit includes having refillable, replaceable, or disposable cartridges and/or a needle assembly for epinephrine injection. A further benefit includes having reliable indicators (e.g., an electronic indicator or a visual check) for providing feedback to a patient on medication.

Other benefits of the described devices include a reservoir design that is collapsible, as illustrated in FIGS. 29A and 29B; that includes electromechanical components (e.g., rotary and linear motors, and solenoids) driven with pulleys, as illustrated in FIGS. 23A-23G; and that is pre-pressurized and released by a trigger, as illustrated in FIGS. 25A and 25B. Further benefits of the reservoir design include having a squeezable pouch, as illustrated in FIGS. 29A and 29B, driven by mechanical or electromechanical components (e.g., rotary or linear motors, pulley systems, springs, pistons, jets, $CO_2$ cartridges); having a nitinol or stainless steel net around the flexible pouch driven by the mechanical and/or electromechanical actuators; and having a fluid inlet for refilling and a fluid outlet for delivery.

Exemplary Device Embodiments for Sensor Module

According to one embodiment A of the sensor module described above, the sensor module is an all-in-one wearable anaphylaxis device. The wearable device is worn, for example, on the thigh, upper arm, or abdomen. The wearable device detects the early onset of anaphylaxis using non-invasive physiological sensors, detection algorithms (e.g., the AOS algorithm), and a histamine biosensor. Optionally, upon detection, the wearable device alerts the user, dials emergency services (e.g., dials "911"), and/or auto-injects epinephrine.

According to another embodiment B of the sensor module described above, the sensor module is a non-invasive wearable device directed to anaphylaxis detection and/or alarm, with no injection and no biosensor. The wearable device is worn, for example, on the thigh, upper arm, or abdomen. The wearable device detects the early onset of anaphylaxis using only non-invasive physiological sensors and detection algorithms (e.g., the AOS algorithm). Optionally, upon detection, the wearable device alerts the user and/or emergency services.

According to an alternative embodiment C of the sensor module described above, the sensor module is a minimally-invasive wearable device for anaphylaxis detection and alarm, with no injection (including only a biosensor). The wearable device is worn, for example, on the thigh, upper arm, or abdomen. The wearable device detects the early onset of anaphylaxis using only a histamine sensor. Optionally, upon detection, the wearable device alerts the user and/or emergency services.

According to another alternative embodiment D of the sensor module described above, the sensor module is a sensor device for continuous monitoring of allergic reactions in a clinical or hospital setting. The sensor device is a real-time histamine sensor that continuously monitors a histamine level in a person's blood or interstitial fluid. The sensor device provides alarms and/or alerts if an allergic reaction is detected.

According to a further alternative embodiment E of the sensor module described above, the sensor module is a wearable manual injector with no sensors. The wearable manual injector is an epinephrine auto-injector device that is worn on the thigh, upper arm, or abdomen (for example). The wearable manual injector is manually activated and, optionally, includes mobile device (e.g., smart phone) integration to notify emergency services (e.g., "911" services) and/or caregivers upon injection. Other options include notifications that the wearable manual injector has a depleted energy level (e.g., the device is in a low battery mode), that the epinephrine has expired or is depleted, etc.

According to a further alternative embodiment F of the sensor module described above, the sensor module is a non-invasive wearable device for continuous asthma monitoring and/or detection (with no injection and no biosensor). The wearable device is worn, for example, on the chest, upper arm, or abdomen, and continuously monitors the breathing of a user. The wearable device assesses the severity of airway obstruction and, upon the early detection of asthmatic conditions, alerts the user and/or others (e.g., caregivers, emergency services, hospital, clinician, family members, etc.). Optionally the wearable device is configured to record airway obstruction severity over time, to detect trends in historical severity data, to alert the user to worsening conditions, and/or to upload the data to a server for analysis by a clinician or other trained personnel.

Each of these embodiments and obvious variations thereof is contemplated as falling within the spirit and scope of the invention. Moreover, the present concepts expressly include any and all combinations and sub-combinations of the preceding elements and aspects.

What is claimed is:

1. A two-step authentication method for detecting and treating symptoms of anaphylaxis or asthma, the method comprising:
    sensing, in a first step, data via one or more non-invasive wearable sensors;
    sending the data to a controller configured with an anaphylaxis detection algorithm;
    extracting by the anaphylaxis detection algorithm, via the controller, a set of features from the data that are relevant to respiration symptoms of a user;
    based on the set of features, calculating by the anaphylaxis detection algorithm, via the controller, an airway obstruction severity ("AOS") score that is associated with the user;
    determining when the AOS score deviates from historical or patient normal values based on the AOS score exceeding a threshold value, the deviation being indicative of anaphylaxis or an asthmatic attack;
    in response to the AOS score exceeding the threshold value, taking a biological sample with a biosensor in a second step subsequent to the first step, the biosensor being separate and distinct from the non-invasive wearable sensors;
    independently confirming from the biological sample that anaphylaxis or the asthmatic attack is occurring; and
    in response to the confirming, triggering a wearable needle to insert an auto-injection of epinephrine.

2. The method of claim 1, wherein the biological sample is blood or interstitial fluid.

3. The method of claim 1, wherein the data is indicative of measured histamine levels.

4. The method of claim 1, further comprising contacting a caregiver or emergency services in response to the auto-injection of epinephrine.

5. The method of claim 1, further comprising contacting a caregiver or emergency services in response to determining occurrence of the anaphylaxis or the asthmatic attack.

6. The method of claim 5, wherein the contacting of the caregiver or emergency services is communicated wirelessly between a communication port and a mobile device.

7. The method of claim 1, wherein the biological sample includes biosensor data indicative of measured histamine levels.

8. The method of claim 1, further comprising moving the wearable needle between a retracted position and an injection position, the retracted position being within an enclosure in which a reservoir stores the epinephrine, the injection position having the wearable needle at least in part outside the enclosure.

9. The method of claim 1, further comprising determining when the AOS score deviates from historical or patient normal values in real-time.

10. A physiologic sensor module for a two-step authentication method of detecting and treating symptoms of anaphylaxis or asthma, the physiologic sensor module comprising:
    one or more non-invasive wearable sensors for sensing data in a first step of detecting and treating anaphylaxis or an asthmatic attack;
    a biosensor separate and distinct from the non-invasive wearable sensors;
    a wearable needle; and
    at least one controller communicatively coupled to the one or more non-invasive wearable sensors, the biosensor, and to the wearable needle, the at least one controller including an anaphylaxis detection algorithm and being configured to:
        receive the data from the one or more non-invasive wearable sensors,
        extract by the anaphylaxis detection algorithm a set of features from the data that are relevant to respiration symptoms of a user,
        based on the set of features, calculate by the anaphylaxis detection algorithm an airway obstruction severity ("AOS") score that is associated with the user,
        determine when the AOS score deviates from historical or patient normal values based on the AOS score exceeding a threshold value, the deviation being indicative of anaphylaxis or an asthmatic attack,
        in response to the AOS score exceeding the threshold value, take a biological sample with the biosensor in a second step subsequent to the first step,
        independently confirm from the biological sample that anaphylaxis or the asthmatic attack is occurring, and
        in response to the confirmation, trigger the wearable needle to insert an auto-injection of epinephrine.

11. The physiologic sensor module of claim 10, wherein the biological sample is blood or interstitial fluid.

12. The physiologic sensor module of claim 10, wherein the data is indicative of measured histamine levels.

13. The physiologic sensor module of claim 10, further comprising a communication port for contacting, via the at least one controller, a caregiver or emergency services in response to the auto-injection of epinephrine.

14. The physiologic sensor module of claim 10, further comprising a communication port for contacting, via the at least one controller, a mobile device of a caregiver or emergency services in response to determining occurrence of the anaphylaxis or the asthmatic attack.

15. The physiologic sensor module of claim 10, wherein the biological sample includes biosensor data indicative of measured histamine levels.

16. The physiologic sensor module of claim 10, further comprising a housing with a reservoir for storing the epinephrine, the wearable needle being enclosed in the housing in a retracted position, the wearable needle being movable at least in part outside the enclosure in an injecting position when the wearable needle inserts the auto-injection of the epinephrine.

* * * * *